US012071653B2

(12) United States Patent
Lee et al.

(10) Patent No.: US 12,071,653 B2
(45) Date of Patent: *Aug. 27, 2024

(54) METHODS AND SYSTEMS FOR NUCLEIC ACID SEQUENCING

(71) Applicant: Ultima Genomics, Inc., Newark, CA (US)

(72) Inventors: Linda Lee, Palo Alto, CA (US); Steven Menchen, Fremont, CA (US); Theo Nikiforov, Carlsbad, CA (US); Gilad Almogy, Palo Alto, CA (US); Florian Oberstrass, Menlo Park, CA (US)

(73) Assignee: Ultima Genomics, Inc., Fremont, CA (US)

( * ) Notice: Subject to any disclaimer, the term of this patent is extended or adjusted under 35 U.S.C. 154(b) by 115 days.

This patent is subject to a terminal disclaimer.

(21) Appl. No.: 17/712,765

(22) Filed: Apr. 4, 2022

(65) Prior Publication Data
US 2022/0348994 A1    Nov. 3, 2022

Related U.S. Application Data

(63) Continuation of application No. 16/822,121, filed on Mar. 18, 2020, now Pat. No. 11,326,203, which is a continuation of application No. PCT/US2018/052980, filed on Sep. 26, 2018.

(60) Provisional application No. 62/564,227, filed on Sep. 27, 2017.

(51) Int. Cl.
*C12Q 1/68* (2018.01)
*C12Q 1/6806* (2018.01)
*C12Q 1/6823* (2018.01)
*C12Q 1/6869* (2018.01)
*G01N 21/64* (2006.01)

(52) U.S. Cl.
CPC ......... *C12Q 1/6823* (2013.01); *C12Q 1/6806* (2013.01); *C12Q 1/6869* (2013.01); *G01N 21/6428* (2013.01); *G01N 2021/6439* (2013.01)

(58) Field of Classification Search
CPC .. C12Q 1/6823; C12Q 1/6806; C12Q 1/6869; G01N 21/6428; G01N 2021/6439
See application file for complete search history.

(56) References Cited

U.S. PATENT DOCUMENTS

| | | | |
|---|---|---|---|
| 5,210,412 A * | 5/1993 | Levis | H01J 49/0463 250/288 |
| 7,223,538 B2 | 5/2007 | Brush et al. | |
| 9,005,892 B2 | 4/2015 | Carell et al. | |
| 9,200,311 B2 | 12/2015 | Otto et al. | |
| 9,217,177 B2 | 12/2015 | McKernan et al. | |
| 9,650,406 B2 | 5/2017 | Zhou et al. | |
| 10,851,410 B2 | 12/2020 | Drmanac et al. | |
| 11,326,203 B2 | 5/2022 | Lee et al. | |
| 2001/0018184 A1* | 8/2001 | Williams | C12Q 1/6874 435/6.12 |
| 2010/0092957 A1 | 4/2010 | Zhao et al. | |
| 2015/0011712 A1 | 1/2015 | Chaix et al. | |
| 2016/0130644 A1 | 5/2016 | Menchen et al. | |

FOREIGN PATENT DOCUMENTS

| | | | |
|---|---|---|---|
| EP | 0447133 B1 | 7/1996 | |
| WO | WO-2006074351 A2 * | 7/2006 | ........... C07H 19/073 |
| WO | WO-2014191981 A1 | 12/2014 | |
| WO | WO-2019067635 A1 | 4/2019 | |

OTHER PUBLICATIONS

Burgers, et al. Stereochemistry of internucleotide bond formation by polynucleotide phosphorylase from Micrococcus luteus. Biochemistry. Feb. 6, 1979;18(3):450-4.
Conway, et al. The covalent attachment of multiple fluorophores to DNA containing phosphorothioate diesters results in highly sensitive detection of single-stranded DNA. Bioconjugate chemistry vol. 2,6 (1991): 452-7.
Dewangan, et al. Hydrolytic cleavage of paraoxon and parathion by oximate and functionalized oximate ions: A comparative study. Indian Journal of Chemistry. vol. 55A (2016): 560-565.
Gish, G, and F Eckstein. DNA and RNA sequence determination based on phosphorothioate chemistry. Science (New York, N.Y.) vol. 240,4858 (1988): 1520-2.
Gut, et al. A procedure for selective DNA alkylation and detection by mass spectrometry, Nucleic Acids Research, 23,8 (1995): 1367-73.
Hodges, et al. Post-Assay Covalent Labeling of Phosphorothioate-Containing Nucleic Acids with Multiple Fluorescent Markers, Biochemistry, 1989, 28:261-67.
Kaboudin, et al. Synthesis of phosphorothioates using thiophosphate salts. Beilstein J Org Chem. 2006; 2: 4.
Kuimelis, et al. Cleavage properties of an oligonucleotide containing a bridged internucleotide 5'- phosphorothioate RNA linkage. Nucleic acids research vol. 23,23 (1995): 4753-60.
Lee, L G et al. DNA sequencing with dye-labeled terminators and T7 Dna polymerase: effect of dyes and dNTPs on incorporation of dye-terminators and probability analysis of termination fragments. Nucleic acids research vol. 20,10 (1992): 2471-83.
Li, et al. Synthesis, properties, and applications of oligonucleotides containing an RNA dinucleotide phosphorothiolate linkage. Accounts of chemical research vol. 44,12 (2011): 1257-69.
Mag et al. Synthesis and selective cleavage of an oligodeoxynucleotide containing a bridged internucleotide 5'-phosphorothioate linkage. Nucleic Acids Res. 19, 7 (1991): 1437-1441.
Nakamaye, et al. Direct sequencing of polymerase chain reaction amplified DNA fragments through the incorporation of deoxynucleoside alpha-thiotriphosphates. Nucleic Acids Res. 16, 21 (1988): 9947-9959.

(Continued)

*Primary Examiner* — Jezia Riley
(74) *Attorney, Agent, or Firm* — Schmidt Patent Law, Inc.

(57) ABSTRACT

The disclosure provides methods for sequencing nucleic acids using, including with nucleotide analogs and subsequently appended labels.

23 Claims, 10 Drawing Sheets

Specification includes a Sequence Listing.

(56) References Cited

OTHER PUBLICATIONS

Nikiforov, et al. Application of Fluorescence Polarization to Enzyme Assays and Single Nucleotide Polymorphism Genotyping: Some Recent Developments. Combinatorial Chemistry & High Throughput Screening. 6 (2003): 201-12.
PCT/US2018/052980 International Search Report and Written Opinion dated Jan. 15, 2019.
Qiao, et al. Novel pyridinium-based tags: synthesis and characterization for highly efficient analysis of thiol-containing peptides by mass spectrometry. The Analyst 140.2 (2015): 407-13.
Reese, Colin B. and Hongbin Yan. An approach to the desulfurization of oligonucleotide phosphorothioates. Tetrahedron Letters 44 (2003): 2501-2504.
Reese, et al. Avoidance of sulfur loss during ammonia treatment of oligonucleotide phosphorothioates. Nucleic Acids Res. 25,14 (1997): 2943-4.
Reese, et al. Oximate ion promoted unblocking of oligonucleotide phosphotriester intermediates. Tetrahedron Letters. 19,30 (1978): 2727-2730.
Reese, et al. Some observations relating to the oximate ion promoted unblocking of oligonucleotide aryl esters. Nucleic Acids Res. 9,18 (1981): 4611-4626.
Toutchkine, et al. Facile synthesis of thiol-reactive Cy3 and Cy5 derivatives with enhanced water solubility. Bioconjugate chemistry. 13,3 (2002): 387-91.
Turcatti, et al. A new class of cleavable fluorescent nucleotides: synthesis and optimization as reversible terminators for DNA sequencing by synthesis. Nucleic Acids Res. 36,4 (2008): e25.
Worek, et al. Kinetic analysis of interactions between human acetylcholinesterase, structurally different organophosphorus compounds and oximes. Biochem Pharmacol. 68,11 (2004): 2237-48.
Wozniak, et al. Potassium peroxymonosulfate (oxone)—an efficient oxidizing agent for phosphothio compounds. Bioorg Med Chem Lett. Oct. 6, 1998;8(19):2641-6.
Wu, et al. Kinetics of coupling reactions that generate monothiophosphate disulfides: implications for modification of RNAs. Bioconjug Chem. Nov.-Dec. 2001;12(6):842-4.
Wyrzykiewicz, et al. Sequencing of oligonucleotide phosphorothioates based on solid-supported desulfurization. Nucleic Acids Research 22, 13 (1994): 2667-69.
Antonijevic, Biljana et al. Unequal efficacy of pyridinium oximes in acute organophosphate poisoning. Clinical medicine & research. vol. 5,1 (2007): 71-82.
Gruber, H. J. et al. Preparation of thiol-reactive Cy5 derivatives from commercial Cy5 succinimidyl ester. Bioconjugate chemistry. vol. 11,2 (2000): 161-6.
Ochtrop, Philipp et al. Recent advances of thiol-selective bioconjugation reactions. Current opinion in chemical biology. vol. 58 (2020): 28-36.
Petri, Laszlo et al. Comparative reactivity analysis of small-molecule thiol surrogates, Bioorganic & Medicinal Chemistry (2020).
Zhang, Yingqian et al. Cysteine-specific protein multi-functionalization and disulfide bridging using 3-bromo-5-methylene pyrrolones. Nat Commun. vol. 11 (2020): 1015.
Zhang, Yingqian et al. Thiol Specific and Tracelessly Removable Bioconjugation via Michael Addition to 5-Methylene Pyrrolones. Journal of the American Chemical Society. vol. 139,17 (2017): 6146-6151.

* cited by examiner

METHODS AND SYSTEMS FOR NUCLEIC ACID SEQUENCING

CROSS-REFERENCE

This application is a continuation of U.S. patent application Ser. No. 16/822,121, filed Mar. 18, 2020, which is a continuation of International Patent Application PCT/US2018/052980, filed Sep. 26, 2018, which claims the benefit of U.S. Provisional Patent Application No. 62/564,227, filed Sep. 27, 2017, each of which application is entirely incorporated herein by reference.

SEQUENCE LISTING

The instant application contains a Sequence Listing which has been submitted electronically in ASCII format and is hereby incorporated by reference in its entirety. Said ASCII copy, created on Jun. 7, 2022, is named 51024-706 302 SL.txt and is 2,412 bytes in size.

BACKGROUND

Sequencing of nucleic acids has various applications in the fields of molecular biology and medicine (e.g., diagnosis). Nucleic acid sequencing may provide information that may be used to diagnose a certain condition in a subject and in some cases tailor a treatment plan. Sequencing is widely used for molecular biology applications, including vector designs, gene therapy, vaccine design, industrial strain design and verification.

Despite the prevalence of nucleic acid sequencing systems and methods, such systems and methods may sequence nucleic acid molecules at error rates that may not be sufficient for diagnostics applications. For example, a high error rate may make it difficult to differentiate sequencing error from a variant (e.g., single nucleotide polymorphism).

SUMMARY

Recognized herein is a need for improved systems and methods of sequencing nucleic acids which minimizes error rates. Systems and methods provided herein can mitigate errors associated with sequencing by reducing or even eliminating errors associated with context dependence during sequencing.

An aspect of the disclosure provides a method for determining a sequence of a template nucleic acid molecule, comprising: (a) generating a reaction mixture comprising the template nucleic acid molecule, a primer capable of hybridizing to the template nucleic acid molecule, and a plurality of free nucleotide analogs, wherein a given free nucleotide analog of the plurality of free nucleotide analogs comprises a functional group; (b) subjecting the reaction mixture to conditions sufficient to conduct a primer extension reaction on the template nucleic acid molecule in presence of the primer, to incorporate the given free nucleotide analog comprising the functional group into a growing nucleic acid strand having sequence complementarity with the template nucleic acid molecule; (c) upon incorporating the given free nucleotide analog into the growing nucleic acid strand, reacting the functional group with a labeling reagent comprising a label to generate a labeled functional group; (d) detecting one or more signals indicative of the labeled functional group; and (e) subjecting the labeled functional group to conditions sufficient to convert the labeled functional group to a moiety that is substantially unreactive with the labeling reagent. In some instances, any unlabeled functional groups that remain may be subject to conditions sufficient to convert them to (or retain them as) moieties that are substantially unreactive with the labeling reagent.

In another aspect, the disclosure provides a method for determining a sequence of a template nucleic acid molecule, comprising: (a) generating a reaction mixture comprising the template nucleic acid molecule, a primer capable of hybridizing to the template nucleic acid molecule, and a plurality of nucleotide analogs, wherein a given nucleotide analog of the plurality of nucleotide analogs comprises a functional group; (b) subjecting the reaction mixture to conditions sufficient to conduct a primer extension reaction on the template nucleic acid molecule in presence of the primer and a polymerizing enzyme that is not a ligase, to incorporate the given nucleotide analog comprising the functional group into a growing nucleic acid strand having sequence complementarity with the template nucleic acid molecule; (c) upon incorporating the given nucleotide analog into the growing nucleic acid strand, reacting the functional group with a labeling reagent comprising a label to generate a labeled functional group; (d) detecting one or more signals indicative of the labeled functional group; and (e) subjecting the labeled functional group to conditions sufficient to convert the labeled functional group to a moiety that is substantially unreactive with the labeling reagent. In some embodiments, the polymerizing enzyme is a polymerase. In some instances, any unlabeled functional groups that remain may be subject to conditions sufficient to convert them to (or retain them as) moieties that are substantially unreactive with the labeling reagent.

In some embodiments, the template nucleic acid molecule is immobilized to a support. In some embodiments, the given support is a bead or a substantially planar surface.

In some embodiments, the functional group comprises sulfur or selenium. In some embodiments, the plurality of free nucleotide analogs comprises alpha-thio-deoxynucleotide triphosphates ($\alpha$-S-dNTPs). In some embodiments, the plurality of free nucleic acid analogs comprises phosphorothioate nucleic acids or phosphoroselenoate nucleic acids. In some embodiments, the functional group in the plurality of nucleotide analogs comprises an azido group. In some cases, the functional group may be an ethynyl group.

In some embodiments, the label is detectable. In some embodiments, the labeling reagent comprises a luminescent moiety. In some embodiments, the labeling reagent comprises an optically-active moiety. In some embodiments, the labeling reagent comprises a dye that is subject to proximity quenching. In some embodiments, the labeling reagent comprises a self-quenching dye or a proximity quenching dye. In some embodiments, the reaction of the functional group with a labeling reagent comprises contacting the functional group with a solution comprising the labeling reagent. In some embodiments, the solution comprises a derivative of the label, wherein the derivative lacks a detectable moiety of the label. In some embodiments, the reaction of the functional group with a label comprises contacting the functional group with an antigen specific for the functional group and capable of coupling to the label.

In some embodiments, the reaction of the functional group with a labeling reagent comprises covalently coupling the label with at least a portion of the functional group. In some embodiments, the reaction of the functional group with a labeling reagent further comprises subjecting the template nucleic acid molecule to one or more washing cycles.

In some embodiments, the reaction of the functional group with a labeling reagent comprises conducting an alkylation reaction using the labeling reagent and the functional group. In some embodiments, the label is derived from Atto-647N-iodoacetamide, an S-pyridyl-containing reagent, Cy5, Cy5-azide, Bodipy FL iodoacetamide, Atto-633-iodoacetamide, tetramethylrhodamine iodoacetamide or Atto-488 iodoacetamide. In some embodiments, the label is derived from the S-pyridyl-containing reagent, and wherein the reaction to convert the labeled functional group to a moiety that is substantially unreactive with the labeling reagent is conducted at a pH of about 4 to about 6. In some embodiments, the label is derived from the S-pyridyl-containing reagent, and wherein the reaction to convert the labeled functional group to a moiety that is substantially unreactive with the labeling reagent is conducted at a pH of about 5 to about 6.

In some embodiments, the reaction of the functional group with a labeling reagent comprises conducting a click reaction. In some cases, the click reaction may be conducted in the presence of an alkyne moiety, an azide moiety and copper(I). In other cases, the click reaction is conducted without copper(I) in the reaction. In some embodiments, the click reaction is conducted in the presence of dibenzocyclooctyne and azide moieties, or trans-cyclooctene and tetrazine moieties. In some embodiments, the click reaction is conducted in the presence of dibenzocyclooctyne.

In some embodiments, the one or more signals indicative of the labeled functional group are optical signals, electrical signals or mechanical signals.

In some embodiments, the functional group comprises sulfur, and wherein the reaction to convert the labeled functional group to a moiety that is substantially unreactive with the labeling reagent comprises conducting a desulfurization reaction. In some embodiments, the reaction comprises contacting the labeled functional group with a metal ion. In some embodiments, the metal ion comprises silver, mercury or lead.

In some embodiments, the reaction to convert the labeled functional group to a moiety that is substantially unreactive with the labeling reagent comprises contacting the labeled functional group with an oxidant. In some embodiments, the oxidant comprises iodine, iodosobenzoate or potassium peroxymonosulfate (oxone).

In some embodiments, the reaction to convert the labeled functional group to a moiety that is substantially unreactive with the labeling reagent comprises contacting the labeled functional group with the conjugate base of an oxime. In some embodiments, the oxime comprises 2-pyridine aldoxime, 4-pyridine aldoxime, obidoxime, HI 6, HLö 7, E-2-nitrobenzaldoxime or E-4-nitrobenzldoxime.

In some embodiments, the labeled functional group comprises a disulfide bond coupling the label to the labeled functional group, and wherein the reaction to convert the labeled functional group to a moiety that is substantially unreactive with the labeling reagent comprises subjecting the disulfide bond to conditions sufficient to reduce the disulfide bond, thereby generating a modified labeled functional group. In some embodiments, the conditions comprise using a reducing agent that comprises Tris(2-carboxyethyl) phosphine (TCEP), tris(hydroxypropyl)phosphine (THP) or dithiothreitol (DTT). In some embodiments, the reaction further comprises contacting the modified labeled functional group with an oxidant.

In some embodiments, the method for determining a sequence of a template nucleic acid molecule further comprises repeating parts of the method at least once using an additional plurality of free nucleotide analogs having an individual free nucleotide analog absent from the plurality of free nucleotide analogs. In some embodiments, the method further comprises determining a nucleic acid sequence of the template nucleic acid molecule from the one or more detected signals.

In some embodiments, the method for determining a sequence of a template nucleic acid molecule further comprises performing parts of the method for a plurality of template nucleic acid molecules using a plurality of primers, wherein a given primer of the plurality of primers is capable of hybridizing to a given template nucleic acid molecule of the plurality of template nucleic acid molecules.

In some embodiments, the reaction to convert the labeled functional group to a moiety that is substantially unreactive with the labeling reagent comprises cleaving the label from the labeled functional group.

In some embodiments, the individual nucleotide analogs of the plurality of nucleotide analogs are of the same type of nucleotide analog.

In some embodiments, the reaction mixture comprises magnesium ion or manganese ion.

In some embodiments, the labeled functional group is substantially unreactive with the labeling reagent.

In some embodiments, the functional group in the nucleotide analog is optically undetectable, wherein in upon incorporation in to the growing nucleic acid strand the labeled functional group is optically detectable, and wherein the moiety resulting from the reaction to convert the labeled functional group to a moiety that is substantially unreactive with the labeling reagent is optically undetectable.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION

Figure 1:
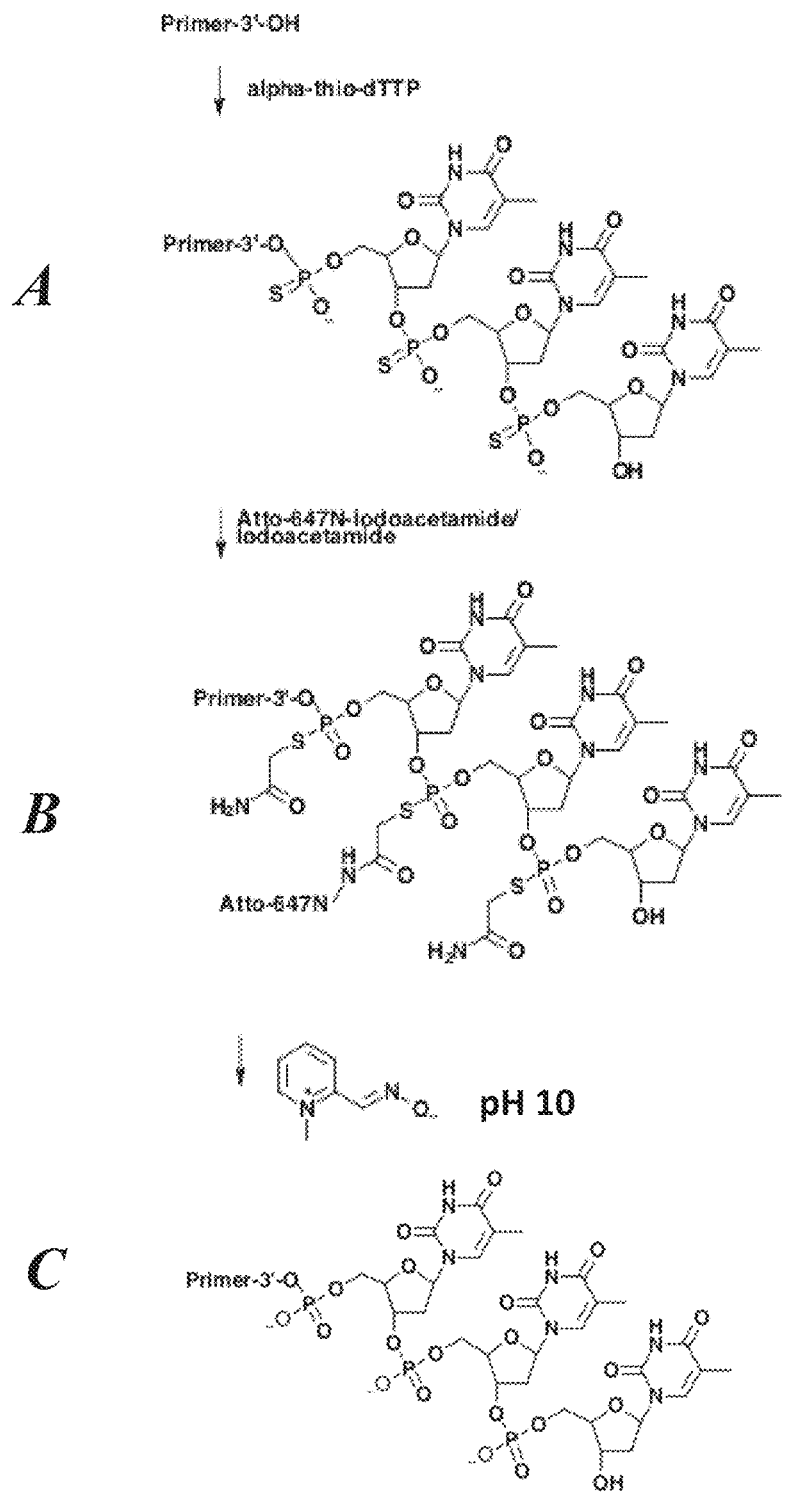
FIG. 1 shows an example sequencing reaction scheme using metal ions.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "sequencing," as used herein, generally refers to a process for generating or identifying a sequence of a biological molecule, such as a nucleic molecule. Such sequence may be a nucleic acid sequence, which may include a sequence of nucleic acid bases. Sequencing may be single molecule sequencing or sequencing by synthesis, for example. Sequencing may be performed using template nucleic acid molecules immobilized on a support, such as a flow cell or one or more beads.

The term "subject," as used herein, generally refers to an individual having a biological sample that is undergoing processing or analysis. A subject can be an animal or plant. The subject can be a mammal, such as a human, dog, cat, horse, pig or rodent. The subject can have or be suspected of having a disease, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease. The subject can have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease.

The term "sample," as used herein, generally refers to a biological sample. Examples of biological samples include nucleic acid molecules, amino acids, polypeptides, proteins, carbohydrates, fats, or viruses. In an example, a biological sample is a nucleic acid sample including one or more nucleic acid molecules, such as deoxyribonucleic acid (DNA) and/or ribonucleic acid (RNA). The nucleic acid molecules may be cell-free or cell-free nucleic acid molecules, such as cell free DNA or cell free RNA. The nucleic acid molecules may be derived from a variety of sources including human, mammal, non-human mammal, ape, monkey, chimpanzee, reptilian, amphibian, or avian, sources. Further, samples may be extracted from variety of animal fluids containing cell free sequences, including but not limited to blood, serum, plasma, vitreous, sputum, urine, tears, perspiration, saliva, semen, mucosal excretions, mucus, spinal fluid, amniotic fluid, lymph fluid and the like. Cell free polynucleotides may be fetal in origin (via fluid taken from a pregnant subject), or may be derived from tissue of the subject itself.

The terms "template nucleic acid", "target nucleic acid", "nucleic acid molecule," "nucleic acid sequence," "nucleic acid fragment," "oligonucleotide" and "polynucleotide," as used herein, generally refer to a polynucleotide that may have various lengths, such as either deoxy ribonucleotides or DNA or ribonucleotides or RNA, or analogs thereof. A nucleic acid molecule can have a length of at least about 10 nucleic acid bases ("bases"), 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. An oligonucleotide is typically composed of a specific sequence of four nucleotide bases: adenine (A); cytosine (C); guanine (G); and thymine (T) (uracil (U) for thymine (T) when the polynucleotide is RNA). Oligonucleotides may include one or more nonstandard nucleotide(s), nucleotide analog(s) and/or modified nucleotides. Non-limiting examples of nucleic acids include DNA, RNA, genomic DNA or synthetic DNA/RNA or coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence and isolated RNA of any sequence.

The term "support" as used herein generally refers to a material having a surface on or to which additional matter can be coupled to or appended. In some cases, a support is a solid support such as a slide, a bead, a resin, a chip, an array, a matrix, a surface of a well, a membrane, a nanopore, a substantially planar surface, or a gel. The solid support may, for example, be a flat substrate (e.g., made of glass, plastic, silicon, etc.) or a magnetic bead The substrate may have surface properties, such as textures, patterns, microstructure coatings, surfactants, or any combination thereof to retain the bead at a given location (such as in a position to be in operative communication with a detector). A support may be in optical communication with a detector, may be physically in contact with the detector, may be separated from the detector by a distance, or any combination thereof. Nucleic acid molecules may be immobilized to the support. A nucleic acid may be attached to an adaptor to facilitate its binding to the support.

The term "primer(s)" refers to a polynucleotide which is complementary to the template nucleic acid. The complementarity or homology or sequence identity between the primer and the template nucleic acid may be limited. The length of the primer may be between 8 nucleotide bases to 50 nucleotide bases. In some cases, the length of the primer may be more than 2 nucleotide bases, more than 3 nucleotide bases, 4 nucleotide bases, 5 nucleotide bases, 6 nucleotide bases, 7 nucleotide bases, 8 nucleotide bases, 9 nucleotide bases, 10 nucleotide bases, 11 nucleotide bases, 12 nucleotide bases, 13 nucleotide bases, 14 nucleotide bases, 15 nucleotide bases, 16 nucleotide bases, 17 nucleotide bases, 18 nucleotide bases, 19 nucleotide bases, 20 nucleotide bases, 21 nucleotide bases, 22 nucleotide bases, 23 nucleotide bases, 24 nucleotide bases, 25 nucleotide bases, 26 nucleotide bases, 27 nucleotide bases, 28 nucleotide bases, 29 nucleotide bases, 30 nucleotide bases, 31 nucleotide bases, 32 nucleotide bases, 33 nucleotide bases, 34 nucleotide bases, 35 nucleotide bases, 37 nucleotide bases, 40 nucleotide bases, 42 nucleotide bases, 45 nucleotide bases, 47 nucleotide bases or 50 nucleotide bases. In some cases, the length of the primer may be less than 50 nucleotide bases, 47 nucleotide bases, 45 nucleotide bases, 42 nucleotide bases, 40 nucleotide bases, 37 nucleotide bases, 35 nucleotide bases, 34 nucleotide bases, 33 nucleotide bases, 32 nucleotide bases, 31 nucleotide bases, 30 nucleotide bases, 29 nucleotide bases, 28 nucleotide bases, 27 nucleotide bases, 26 nucleotide bases, 25 nucleotide bases, 24 nucleotide bases, 23 nucleotide bases, 22 nucleotide bases, 21 nucleotide bases, 20 nucleotide bases, 19 nucleotide bases, 18 nucleotide bases, 17 nucleotide bases, 16 nucleotide bases, 15 nucleotide bases, 14 nucleotide bases, 13 nucleotide bases, 12 nucleotide bases, 11 nucleotide bases, 10 nucleotide bases, 9 nucleotide bases, 8 nucleotide bases, 7 nucleotide bases, 6 nucleotide bases, 5 nucleotide bases, 4 nucleotide bases, 3 nucleotide bases or 2 nucleotide bases.

A primer may exhibit sequence identity or homology or complementarity to the template nucleic acid. The homology or sequence identity or complementarity between the primer and a template nucleic acid may be based on the length of the primer. For example, if the primer length is about 20 nucleic acids, it may contain 10 or more contiguous nucleic acid bases complementary to the template nucleic acid.

As used herein, the term "primer extension reaction" generally refers to the, binding of a primer to a strand of the template nucleic acid, followed by elongation of the primer(s). It may also include, denaturing of a double-stranded nucleic acid and the binding of a primer strand to either one or both of the denatured template nucleic acid strands, followed by elongation of the primer(s). Primer extension reactions may be used to incorporate nucleotides or nucleotide analogs to a primer in template-directed fashion by using enzymes (polymerizing enzymes).

As used herein the term "nucleotide analogs" may include, but are not limited to diaminopurine, 5-fluorouracil, 5-bromouracil, 5-chlorouracil, 5-i odouracil, hypoxanthine, xantine, 4-acetyl cytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl) uracil, (acp3)w, 2,6-diaminopurine, ethynyl nucleotide bases, 1-propynyl nucleotide bases, azido nucleotide bases, phosphoroselenoate nucleic acids and the like. In some cases, nucleotides may include modifications in their phosphate moieties, including modifications to a triphosphate moiety. Additional, non-limiting examples of modifications include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates) or modifications with selenium moieties (e.g., phosphoroselenoate nucleic acids). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Nucleotide analogs may be capable of reacting or bonding with detectable moieties for nucleotide detection.

The term "free nucleotide analog" as used herein, generally refers to a nucleotide analog that is not coupled to an additional nucleotide or nucleotide analog. Free nucleotide analogs may be incorporated in to the growing nucleic acid chain by primer extension reactions.

The term "polymerizing enzyme," as used herein, generally refers to any enzyme capable of catalyzing a polymerization reaction. A polymerizing enzyme may be used to extend primers with the incorporation of nucleotides or nucleotide analogs. In some cases, a polymerizing enzyme is a polymerase. Examples of polymerases include, without limitation, a nucleic acid polymerase ("polymerase"). The polymerase can be naturally occurring or synthesized. In some cases, a polymerase has relatively high processivity, namely the capability of the polymerase to consecutively incorporate nucleotides into a nucleic acid template without releasing the nucleic acid template. In some cases, a polymerizing enzyme is a transcriptase. Examples of polymerases include a DNA polymerase, an RNA polymerase, a thermostable polymerase, a wild-type polymerase, a modified polymerase, *E. coli* DNA polymerase I, T7 DNA polymerase, bacteriophage T4 DNA polymerase, Φ29 (phi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some cases, the polymerase is a single subunit polymerase.

The term "label" as used herein generally refers to a moiety that is capable of coupling with a species, such as, for example a nucleotide analog. In some cases, a label may be a detectable label that emits a signal (or reduces an already emitted signal) that can be detected. In some cases, such a signal may be indicative of incorporation of one or more nucleotides or nucleotide analogs. In some cases, a label may be coupled to a nucleotide or nucleotide analog, which nucleotide or nucleotide analog may be used in a primer extension reaction. In some cases, the label may be coupled to a nucleotide analog after the primer extension reaction. The label, in some cases, may be reactive specifically with a nucleotide or nucleotide analog. Coupling may be covalent or non-covalent (e.g., via ionic interactions, Van der Waals forces, etc.). In some cases, coupling may be via a linker, which may be cleavable, such as photo-cleavable (e.g., cleavable under ultra-violet light), chemically-cleavable (e.g., via a reducing agent, such as dithiothreitol (DTT), tris(2-carboxyethyl)phosphine (TCEP), tris(hydroxypropyl) phosphine (THP) or enzymatically cleavable (e.g., via an esterase, lipase, peptidase or protease). In some cases, the label may be luminescent; that is, fluorescent or phosphorescent. Labels may be quencher molecules. The term "quencher" as used herein generally refers to molecules that can reduce an emitted signal. For example, a template nucleic acid molecule may be designed to emit a detectable signal. Incorporation of a nucleotide or nucleotide analog comprising a quencher can reduce or eliminate the signal, which reduction or elimination is then detected. In some cases, as described elsewhere herein, labeling with a quencher can occur after nucleotide or nucleotide analog incorporation. Non-limiting examples of dyes include SYBR green, SYBR blue, DAPI, propidium iodine, Hoechst, SYBR gold, ethidium bromide, acridine, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5- (or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores, Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; Cy5Q and Cy7Q and Dark Cyanine dyes (GE Healthcare); Dy-Quenchers (Dyomics), such as DYQ-660 and DYQ-661; and ATTO fluorescent quenchers (ATTO-TEC GmbH), such as ATTO 540Q, 580Q, 612Q. In some cases, the label may be one with linkers. For instance, a label may have a disulfide linker attached to the label. Non-limiting examples of such labels include Cy5-azide, Cy-2-azide, Cy-3-azide, Cy-3.5-azide, Cy5.5-azide and Cy-7-azide. In some cases, a linker may be a cleavable linker. In some cases, the label may be a type that does not self-quench or exhibit proximity quenching. Non-limiting examples of a label type that does not self-quench or exhibit proximity quenching include Bimane derivatives such as Monobromobimane. Alternatively, the label may be a type that self-quenches or exhibits proximity quenching. Non-limiting examples of such labels include Cy5-azide, Cy-2-azide, Cy-3-azide, Cy-3.5-azide, Cy5.5-azide and Cy-7-azide.

The term "proximity quenching" as used herein generally refers to a phenomenon where one or more dyes near each other may exhibit lower fluorescence as compared to the fluorescence they exhibit individually. In some cases, the dye may be subject to proximity quenching wherein the donor dye and acceptor dye are within 1 nm to 50 nm of each other.

The term "detector" as used herein generally refers to a device that is capable of detecting a signal, including a signal indicative of the presence or absence of an incorporated nucleotide or nucleotide analog. In some cases, a detector can include optical and/or electronic components that can detect signals. The term "detector" may be used in detection methods. Non-limiting examples of detection methods include optical detection, spectroscopic detection, electrostatic detection, electrochemical detection, and the like. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

Methods for Sequencing

The present disclosure provides methods for sequencing a target nucleic acid molecule incorporating bases that are complementary to a sequence with the aid of primers. Such incorporation may be performed using an enzyme, such as, for example, a polymerizing enzyme (or polymerase). In some cases, nucleotide analogs containing functional groups may be incorporated. The functional groups may be labeled with detectable moieties to detect the incorporation and the detection of the target nucleic acid. The detectable moieties may be different. After detection, the labeled functional group may be removed and the sequencing reaction may be continued, such as by repeating the previous operations, to detect the sequence of at least a portion of the remaining target nucleic acid.

Methods described herein can be useful for reducing errors associated with context dependence during nucleotide incorporation. In an example, methods described herein can reduce or minimize context dependent errors associated with the incorporation of pre-labeled nucleotides during primer extension reactions by shifting labeling of nucleotides to post-nucleotide incorporation.

In an aspect, disclosed herein are methods for determining a sequence of a template nucleic acid molecule. The template nucleic acid molecule may be part of or suspected of being part of a sample obtained, for example, from a subject.

A method for determining a sequence of a template nucleic acid molecule may comprise generating a reaction mixture comprising a template nucleic acid molecule, a primer capable of hybridizing to the template nucleic acid molecule, and a plurality of free nucleotide analogs, the nucleotide analogs comprise a functional group. The reaction mixture may be subjected to conditions sufficient to conduct a primer extension reaction on the template nucleic acid molecule in presence of the primer, to incorporate the free nucleotide analogs comprising the functional group into a growing nucleic acid strand having sequence complementarity with the template nucleic acid molecule. Upon incorporating the given free nucleotide analog into the growing nucleic acid strand, the functional group may be subjected to a reaction with a labeling reagent that comprises a label to generate a labeled functional group. The labeled functional group may be detected using one or more signals indicative of the labeled functional group. Next, the labeled functional group may be subjected to conditions sufficient to convert the label to a moiety that is substantially unreactive with the labeling reagent.

Another method for determining a sequence of a template nucleic acid molecule may comprise generating a reaction mixture comprising said template nucleic acid molecule, a primer capable of hybridizing to said template nucleic acid molecule, and a plurality of nucleotide analogs, wherein a given nucleotide analog of said plurality of nucleotide analogs comprises a functional group. The reaction mixture may be subjected to conditions sufficient to conduct a primer extension reaction on the template nucleic acid molecule in presence of the primer and a polymerizing enzyme that is not a ligase, to incorporate nucleotide analog(s) comprising the functional group into a growing nucleic acid strand having sequence complementarity with the template nucleic acid molecule. Upon incorporating the nucleotide analog(s) into the growing nucleic acid strand, reacting the functional group with a labeling reagent that comprises a label to generate a labeled functional group. The labeled group may be detected using one or more signals indicative of the labeled functional group. Next, the labeled functional group may be subjected to conditions sufficient to convert the labeled functional group to a moiety that is substantially unreactive with the labeling reagent.

The polymerizing enzyme may be a polymerase, with examples of such a polymerase provided elsewhere herein. For example, the polymerase is a phi29 polymerase or variant thereof.

The template nucleic acid molecule may be immobilized to a support. The support may be any suitable support, including a type of support described elsewhere herein. In some cases, the support is a bead or is a substantially planar surface.

A single primer may hybridize to the template nucleic acid and may be used in the primer extension reaction. The primer extension reaction may be performed on a plurality of template nucleic acid molecules using a plurality of primers. In some cases, a primer from the plurality of primers is capable of hybridizing to a template nucleic acid molecule from the plurality of template nucleic acid molecules.

The primer extension reaction mixture may comprise free nucleotide analogs. In some cases, the primer extension reaction mixture comprises a mixture of free nucleotides, e.g., dinucleotide triphosphates (dNTPs) and free nucleotide analogs. For instance, the nucleotides may be 100% nucleotide analogs or they may be a mixture of modified nucleic acid analogs and unmodified nucleotides (e.g., dNTPs). In some cases, a mixture of natural nucleotides (e.g., dNTPs) and nucleotide analogs may be used in the primer extension reaction. In some examples, the mixture contains 10% dNTPs and 90% nucleotide analogs, 15% dNTPs and 85% nucleotide analogs, 20% dNTPs and 80% nucleotide analogs, 25% dNTPs and 75% nucleotide analogs, 30% dNTPs and 70% nucleotide analogs, 35% dNTPs and 65% nucleotide analogs, 40% dNTPs and 60% nucleotide analogs or 50% dNTPs and 50% nucleotide analogs. In some cases, more than one type of nucleotide analogs may be present in the reaction mixture such as the nucleotide analogs presented elsewhere herein.

In some examples, the mixture of unmodified nucleotides and nucleotide analogs comprises at least 10% nucleotide analogs, at least 20% nucleotide analogs, at least 30% nucleotide analogs, at least 40% nucleotide analogs, at least 50% nucleotide analogs, at least 60% nucleotide analogs, at least 70% nucleotide analogs, at least 80% nucleotide analogs, at least 85% nucleotide analogs, at least 90% nucleotide analogs, or at least 95% nucleotide analogs. A remainder of the mixture may comprise unmodified nucleotides (e.g., dNTPs). The nucleotide analogs may be modified nucleotide analogs.

In some cases, the mixture of free nucleotide analogs may include a plurality of types of nucleotide analogs. For instance, the primer extension reaction may be performed with two types of nucleotide analogs, e.g., ethynyl nucleotide bases, 1-propynyl nucleotide bases, or other suitable nucleotide analogs presented elsewhere herein. In some examples, the mixture contains 10% of a first type of nucleotide analogs and 90% of a second type of nucleotide analogs, 15% of a first type of nucleotide analogs and 85% of a second type of nucleotide analogs, 20% of a first type of nucleotide analogs and 80% of a second type of nucleotide analogs, 25% of a first type of nucleotide analogs and 75% of a second type of nucleotide analogs, 30% of a first type of nucleotide analogs and 70% of a second type of nucleotide analogs, 35% of a first type of nucleotide analogs and 65% of a second type of nucleotide analogs, 40% of a first type of nucleotide analogs and 60% of a second type of nucleotide analogs or 50% of a first type of nucleotide analogs and 50% of a second type of nucleotide analogs. In some cases, more than one type of second type of nucleotide analogs may be present in the reaction mixture such as the second type of nucleotide analogs presented elsewhere herein.

In some examples, the mixture of first type of nucleotides and second type of nucleotide analogs comprises at least 10% of a second type of nucleotide analogs, at least 20% of a second type of nucleotide analogs, at least 30% of a second type of nucleotide analogs, at least 40% of a second type of nucleotide analogs, at least 50% of a second type of nucleotide analogs, at least 60% of a second type of nucleotide analogs, at least 70% of a second type of nucleotide analogs, at least 80% of a second type of nucleotide analogs, at least 85% of a second type of nucleotide analogs, at least 90% of a second type of nucleotide analogs, or at least 95% of a second type of nucleotide analogs.

The mixture may include modified and unmodified nucleotides. As an alternative, the mixture may include naturally occurring and unnatural nucleotides. The mixture may include nucleotides of a given type (e.g., adenosine). In such a case, the mixture may include, for example, modified and unmodified nucleotides of the given type, or naturally and unnaturally occurring nucleotides of the given type.

In some examples, the mixture of unmodified nucleotides and nucleotide analogs comprises at most 99% nucleotide analogs, at most 95% nucleotide analogs, at most 85% nucleotide analogs, at most 80% nucleotide analogs, at most 70% nucleotide analogs, at most 60% nucleotide analogs, at most 50% nucleotide analogs, at most 40% nucleotide analogs, at most 30% nucleotide analogs, at most 20% nucleotide analogs, or at most 15% nucleotide analogs, or at most 10% nucleotide analogs.

The functional group in the nucleotide analogs may comprise sulfur. The sulfur containing free nucleotide analogs may be alpha-thio-deoxynucleotide triphosphates ($\alpha$-S-dNTPs) or as described elsewhere herein. As an alternative, the functional group in the nucleotide analogs may comprise selenium. The selenium containing free nucleotide analogs may be phosphoroselenoate nucleic acids or as described elsewhere herein. The functional group in the nucleotide analogs may comprise azido groups such as ethynyl or 1-propynyl groups.

The individual nucleotide analogs in the primer extension reaction mixture may be of the same type of nucleotide analog. For instance, a primer extension reaction mixture may be performed where the nucleotide analogs include just 2'-Deoxythymidine-5'-O-1-Thiotriphosphates ($\alpha$-S-dTTPs) or just 2'-Deoxycytosine-5'-O-1-Thiotriphosphates ($\alpha$-S-dCTPs) or 2'-Deoxyguanine-5'-O-1-Thiotriphosphates ($\alpha$-S-dGTPs) or 2'-Deoxyadenosine-5'-O-1-Thiotriphosphates ($\alpha$-S-dATPs). In another example, a primer extension reaction mixture may be performed where the nucleotide analogs include just 2'-Se-thymidine-phosphoramidite ($\alpha$-Se-dTTPs), or 2'-Se-adenosine-phosphoramidite ($\alpha$-Se-dATPs), or 2'-Se-cytosine-phosphoramidite ($\alpha$-Se-dCTPs), or 2'-Se-guanine-phosphoramidite ($\alpha$-Se-dGTPs). In some examples, the nucleotide analog is undetectable.

The primer extension reaction may incorporate one free nucleotide analog in to the growing nucleic acid strand. Alternatively, the primer extension reaction may incorporate multiple free nucleotide analogs in to the growing nucleic acid strand. For instance, in case of a homopolymer, multiple free nucleotides may be incorporated. In some cases, the primer extension may be performed with buffers comprising Manganese ion (Mn 2+) or Magnesium ion (Mg 2+).

The primer extension reaction may be followed by one or more wash cycles. The wash cycles may comprise using various wash buffers. The wash buffer may comprise a surfactant. The surfactant may be a non-ionic surfactant, such as, e.g., Triton X-100, Brij 35, Tween 20, Tween 80, CHAPS, Polysorbate 80. In some examples, the amount of surfactant in the wash buffer may be about 0.01% to about 0.1%. In some examples, the amount of surfactant in the wash buffer may be at least about 0.02%. In some examples, the amount of surfactant in the wash buffer may be at most about 0.1%. In some examples, the amount of surfactant in the wash buffer may be about 0.02% to about 0.03%, about 0.01% to about 0.04%, about 0.02% to about 0.05%, about 0.02% to about 0.06%, about 0.02% to about 0.07%, about 0.02% to about 0.08%, about 0.02% to about 0.09%, about 0.02% to about 0.1%, about 0.03% to about 0.04%, about 0.03% to about 0.05%, about 0.03% to about 0.06%, about 0.03% to about 0.07%, about 0.03% to about 0.08%, about 0.03% to about 0.09%, about 0.03% to about 0.1%, about 0.04% to about 0.05%, about 0.04% to about 0.06%, about 0.04% to about 0.07%, about 0.04% to about 0.08%, about 0.04% to about 0.09%, about 0.04% to about 0.1%, about 0.05% to about 0.06%, about 0.05% to about 0.07%, about 0.05% to about 0.08%, about 0.05% to about 0.09%, about 0.05% to about 0.1%, about 0.06% to about 0.07%, about 0.06% to about 0.08%, about 0.06% to about 0.09%, about 0.06% to about 0.1%, about 0.07% to about 0.08%, about 0.07% to about 0.09%, about 0.07% to about 0.1%, about 0.08% to about 0.09%, about 0.08% to about 0.1%, or about 0.09% to about 0.1%. The amount of surfactant in the wash buffer may be about 0.01%, about 0.02%, about 0.03%, about 0.04%, about 0.05%, about 0.06%, about 0.07%, about 0.08%, about 0.09%, or about 0.1%. In some cases, the amount of surfactant in the wash buffer may be at least about 0.01%, at least about 0.02%, at least about 0.03%, at least about 0.04%, at least about 0.05%, at least about 0.06%, at least about 0.07%, at least about 0.08%, at least about 0.09%, at least about 0.1%, at least about 0.5%, at least about 1%, at least about 5%, or at least about 10%. In some cases, the amount of surfactant in the wash buffer may be at most about 10%, at most about 5%, at most about 1%, at most about 0.5%, at most about 0.1%, at most about 0.09%, at most about 0.08%, at most about 0.07%, at most about 0.06%, at most about 0.05%, at most about 0.04%, at most about 0.03%, at most about 0.02%, or at most about 0.01%.

The nucleotide analogs may be labeled after incorporation in to the growing nucleic acid strand. The label may be any suitable label, including a type of label described elsewhere herein. Alternatively, the free nucleotide analogs may be labeled before incorporation in to the growing nucleic acid strand. In some cases, the coupling of the label to the nucleotide analog may be covalent or non-covalent (e.g., via ionic interactions, Van der Waals forces, etc.).

The functional group may be contacted with an antigen specific for the functional group. In some cases, the antigen may be capable of coupling to a label. The antigen may be any suitable antigen capable of reacting with the nucleotide analog and a label. The label may be any suitable label capable of reacting with the antigen and may include examples presented elsewhere herein. In some cases, the coupling of the antigen to the nucleotide analog or the coupling of the antigen to the label may be covalent or non-covalent (e.g., via ionic interactions, Van der Waals forces, etc.). In some cases, the functional group may be contacted with a solution which may comprise a derivative of a label. The derivative may lack a detectable moiety of the label.

The label may be detectable. In some cases, the label may be a luminescent or an optically active moiety. The luminescent or optically active moiety may be dyes presented elsewhere herein. In some cases, the luminescent or optically active dyes may be fluorescent.

The label may comprise a self-quenching dye or a dye that is subject to proximity quenching. The dye may be any suitable dye, including a type of dye described elsewhere herein. Non-limiting examples of dyes are Atto-647N-iodoacetamide, Bodipy FL iodoacetamide, Monobromobimane, Atto-633-iodoacetamide, tetramethylrhodamine iodoacetamide or Atto-488 iodoacetamide, Cy5-azide, Cy-2-azide, Cy-3-azide, Cy-3.5-azide, Cy5.5-azide and Cy-7-azide, Atto 488-azide, Atto 532-azide, Atto 633-azide or 647N-azide.

The label may comprise a dye that is subject to proximity quenching. In some examples, the dye may be subject to proximity quenching wherein the distance between the donor dye and acceptor dye is about 1 nm to about 50 nm. In some examples, the dye may be subject to proximity quenching wherein the distance between the donor dye and acceptor dye is at least about 1 nm, 2 nm, 5 nm, 10 nm, 15 nm, 20 nm, 25 nm, 30 nm, 40 nm or 49 nm. In some examples, the dye may be subject to proximity quenching wherein the distance between the donor dye and acceptor dye is at most about 50 nm, 40 nm, 35 nm, 30 nm, 25 nm, 20 nm, 15 nm, 10 nm, 5 nm or 2 nm. In some examples, the dye may be subject to proximity quenching wherein the distance between the donor dye and acceptor dye is about 1 nm to about 2 nm, about 1 nm to about 5 nm, about 1 nm to about 10 nm, about 1 nm to about 15 nm, about 1 nm to about 20 nm, about 1 nm to about 25 nm, about 1 nm to about 30 nm, about 1 nm to about 40 nm, about 1 nm to about 50 nm, about 2 nm to about 5 nm, about 2 nm to about 10 nm, about 2 nm to about 15 nm, about 2 nm to about 20 nm, about 2 nm to about 25 nm, about 2 nm to about 30 nm, about 2 nm to about 40 nm, about 2 nm to about 50 nm, about 5 nm to about 10 nm, about 5 nm to about 15 nm, about 5 nm to about 20 nm, about 5 nm to about 25 nm, about 5 nm to about 30 nm, about 5 nm to about 40 nm, about 5 nm to about 50 nm, about 10 nm to about 15 nm, about 10 nm to about 20 nm, about 10 nm to about 25 nm, about 10 nm to about 30 nm, about 10 nm to about 40 nm, about 10 nm to about 50 nm, about 15 nm to about 20 nm, about 15 nm to about 25 nm, about 15 nm to about 30 nm, about 15 nm to about 40 nm, about 15 nm to about 50 nm, about 20 nm to about 25 nm, about 20 nm to about 30 nm, about 20 nm to about 40 nm, about 20 nm to about 50 nm, about 25 nm to about 30 nm, about 25 nm to about 40 nm, about 25 nm to about 50 nm, about 30 nm to about 40 nm, about 30 nm to about 50 nm, or about 40 nm to about 50 nm. In some examples, the dye may be subject to proximity quenching wherein the distance between the donor dye and acceptor dye is about 1 nm, about 2 nm, about 5 nm, about 10 nm, about 15 nm, about 20 nm, about 25 nm, about 30 nm, about 40 nm, or about 50 nm.

The functional group may be subjected to a reaction with a label to generate a labeled functional group. In some cases, the reaction may be an alkylation reaction.

In some cases, the alkylation reaction may comprise subjecting the functional group to a labeling reaction with a fluorescent reagent until the alkylation reaction is substantially complete. Substantial completion of a reaction, including an alkylation reaction or other type of reaction described herein, can include reactions that are at least about 80%, 90%, 95%; 99%; or 99.9% complete. For alkylation reactions, completion can be measured with respect to a remaining number of the sites available for alkylation after an alkylation reaction is performed.

The labeling reaction may comprise a mixture of fluorescent reagents and non-fluorescent alkylating reagents. In some cases, a fluorescent dye is functionalized with an iodoacetamide moiety. Examples of fluorescent alkylating reagents are described elsewhere herein and include Atto-647N-iodoacetamide, Atto-633-iodoacetamide, monobromobimane, tetramethylrhodamine iodoacetamide, Atto-488 iodoacetamide or Bodipy FL iodoacetamide. In some cases, the non-fluorescent alkylating reagents may be present in the reaction mixture detached from the fluorescent alkylating reagents, such as the reagent, iodoacetamide. In some cases, the fluorescent alkylating reagents may be self-quenching or proximity quenching optically active dyes examples of which are presented elsewhere herein. In some examples, the label may be derived from Atto-647N-iodoacetamide, an S-pyridyl-containing reagent, monobromobimane, Atto-633-iodoacetamide, Bodipy FL iodoacetamide, tetramethylrhodamine iodoacetamide or Atto-488 iodoacetamide. In some cases, the label may be derived from S-pyridyl-containing reagents.

The alkylation reaction may be performed at a pH of about 3 to about 7.5. In some examples, the alkylation reaction may be performed at a pH of at least about 3, 4, 5, 6, 6.5, 7, 7.5, or 8. In some examples, the alkylation reaction may be performed at a pH of at most about 8, 7.5, 7, 6.5, 6, 5, or 4. In some cases, the alkylation reaction may be performed at a pH of about 3 to about 3.5, about 3 to about 4, about 3 to about 4.5, about 3 to about 5, about 3 to about 5.5, about 3 to about 6, about 3 to about 6.5, about 3 to about 7, about 3 to about 7.5, about 3.5 to about 4, about 3.5 to about 4.5, about 3.5 to about 5, about 3.5 to about 5.5, about 3.5 to about 6, about 3.5 to about 6.5, about 3.5 to about 7, about 3.5 to about 7.5, about 4 to about 4.5, about 4 to about 5, about 4 to about 5.5, about 4 to about 6, about 4 to about 6.5, about 4 to about 7, about 4 to about 7.5, about 4.5 to about 5, about 4.5 to about 5.5, about 4.5 to about 6, about 4.5 to about 6.5, about 4.5 to about 7, about 4.5 to about 7.5, about 5 to about 5.5, about 5 to about 6, about 5 to about 6.5, about 5 to about 7, about 5 to about 7.5, about 5.5 to about 6, about 5.5 to about 6.5, about 5.5 to about 7, about 5.5 to about 7.5, about 6 to about 6.5, about 6 to about 7, about 6 to about 7.5, about 6.5 to about 7, about 6.5 to about 7.5, or about 7 to about 7.5. In some cases, the alkylation reaction may be performed at a pH of about 3, about 3.5, about 4, about 4.5, about 5, about 5.5, about 6, about 6.5, about 7, or about 7.5.

The functional group may be subjected to a reaction with a label to generate a labeled functional group. In some cases, the reaction may be a click reaction. The click reaction may involve using a pair of reagents, a first reagent attached to a label and a second reagent attached to a nucleotide. The pairs may be any suitable pairs for reactions. Non-limiting examples include Copper(I) catalyzed click: Azide/alkyne reagents; copper-free click: dibenzocyclooctyne(DBCO)/azide; and another copper-free click: TCO (trans-cyclooctene/tetrazine). The click reaction may be a copper click reaction that comprises the use of copper. Alternatively, the click reaction may be a different click reaction which does not comprise the use of copper. Such reactions may comprise the use of reagents with strained cyclooctenes such as trans-cyclooctene which may react with tetrazines, or cyclooctyne moieties, e.g., dibenzocyclooctyne, which may react with azides.

In some cases, the click reaction may comprise subjecting the functional group to a labeling reaction with a fluorescent reagent until the click reaction is substantially complete. Substantial completion of a reaction, including a click reaction or other type of reaction described herein, can include reactions that are at least about 80%, 90%, 95%; 99%; or 99.9% complete. For click reactions, completion can be measured with respect to a remaining number of the sites available for a click reaction after a click reaction is performed.

The labeling reaction may be followed by one or more wash cycles. The wash cycles may comprise using various wash buffers. The wash buffer may comprise surfactants, e.g., Triton X-100. Suitable surfactant buffers described for washing cycles after primer extension reactions are equally useful for washing after a labeling reaction.

The washing solution may comprise solvents. In some examples, the solvent in a washing solution may be an organic solvent e.g., acetonitrile, ethanol, methanol, Dimethyl sulfoxide, Dimethylformamide or N-methylpyrrolidone. In some examples, the amount of solvents in the wash buffer may be about 10% to about 100%. In some examples, the amount of solvents in the wash buffer may be at least about 10%, 20%, 25%, 30%, 35%, 40%, 50%, 60%, 70%, 80%, 90% or 99%. In some examples, the amount of solvents in the wash buffer may be at most about 100%, 90%, 80%, 70%, 60%, 50%, 40%, 35%, 30%, 25%, 20% or 9%. In some examples, the amount of solvents in the wash buffer may be about 10% to about 20%, about 10% to about 25%, about 10% to about 30%, about 10% to about 35%, about 10% to about 40%, about 10% to about 50%, about 10% to about 60%, about 10% to about 70%, about 10% to about 80%, about 10% to about 90%, about 10% to about 100%, about 20% to about 25%, about 20% to about 30%, about 20% to about 35%, about 20% to about 40%, about 20% to about 50%, about 20% to about 60%, about 20% to about 70%, about 20% to about 80%, about 20% to about 90%, about 20% to about 100%, about 25% to about 30%, about 25% to about 35%, about 25% to about 40%, about 25% to about 50%, about 25% to about 60%, about 25% to about 70%, about 25% to about 80%, about 25% to about 90%, about 25% to about 100%, about 30% to about 35%, about 30% to about 40%, about 30% to about 50%, about 30% to about 60%, about 30% to about 70%, about 30% to about 80%, about 30% to about 90%, about 30% to about 100%, about 35% to about 40%, about 35% to about 50%, about 35% to about 60%, about 35% to about 70%, about 35% to about 80%, about 35% to about 90%, about 35% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, or about 90% to about 100%. In some examples, the amount of solvents in the wash buffer may be about 10%, about 20%, about 25%, about 30%, about 35%, about 40%, about 50%, about 60%, about 70%, about 80%, about 90%, or about 100%.

The washing solution may comprise buffering agents. In some examples, the buffering agents may be volatile buffering agents, e.g., triethylammonium acetate. In some examples, the amount of buffering agents in the wash buffer may be about 0.01 M to about 0.25 M. In some examples, the amount of buffering agents in the wash buffer may be at least about 0.01 M, 0.03 M, 0.05 M, 0.08 M, 0.1 M, 0.12 M, 0.5 M, 0.18 M, 0.2 M, 0.22 M or 0.24 M. In some examples, the amount of buffering agents in the wash buffer may be at most about 0.25 M, 0.22 M, 0.2 M, 0.18 M, 0.15 M, 0.13 M, 0.1 M, 0.08 M, 0.05 M, 0.03 M or 0.02 M. In some examples, the amount of buffering agents in the wash buffer may be about 0.01 M to about 0.03 M, about 0.01 M to about 0.05 M, about 0.01 M to about 0.08 M, about 0.01 M to about 0.1 M, about 0.01 M to about 0.12 M, about 0.01 M to about 0.15 M, about 0.01 M to about 0.18 M, about 0.01 M to about 0.2 M, about 0.01 M to about 0.22 M, about 0.01 M to about 0.25 M, about 0.03 M to about 0.05 M, about 0.03 M to about 0.08 M, about 0.03 M to about 0.1 M, about 0.03 M to about 0.12 M, about 0.03 M to about 0.15 M, about 0.03 M to about 0.18 M, about 0.03 M to about 0.2 M, about 0.03 M to about 0.22 M, about 0.03 M to about 0.25 M, about 0.05 M to about 0.08 M, about 0.05 M to about 0.1 M, about 0.05 M to about 0.12 M, about 0.05 M to about 0.15 M, about 0.05 M to about 0.18 M, about 0.05 M to about 0.2 M, about 0.05 M to about 0.22 M, about 0.05 M to about 0.25 M, about 0.08 M to about 0.1 M, about 0.08 M to about 0.12 M, about 0.08 M to about 0.15 M, about 0.08 M to about 0.18 M, about 0.08 M to about 0.2 M, about 0.08 M to about 0.22 M, about 0.08 M to about 0.25 M, about 0.1 M to about 0.12 M, about 0.1 M to about 0.15 M, about 0.1 M to about 0.18 M, about 0.1 M to about 0.2 M, about 0.1 M to about 0.22 M, about 0.1 M to about 0.25 M, about 0.12 M to about 0.15 M, about 0.12 M to about 0.18 M, about 0.12 M to about 0.2 M, about 0.12 M to about 0.22 M, about 0.12 M to about 0.25 M, about 0.15 M to about 0.18 M, about 0.15 M to about 0.2 M, about 0.15 M to about 0.22 M, about 0.15 M to about 0.25 M, about 0.18 M to about 0.2 M, about 0.18 M to about 0.22 M, about 0.18 M to about 0.25 M, about 0.2 M to about 0.22 M, about 0.2 M to about 0.25 M, or about 0.22 M to about 0.25 M. In some examples, the amount of buffering agents in the wash buffer may be about 0.01 M, about 0.03 M, about 0.05 M, about 0.08 M, about 0.1 M, about 0.12 M, about 0.15 M, about 0.18 M, about 0.2 M, about 0.22 M, or about 0.25 M.

The method may comprise detecting one or more signals indicative of the labeled functional groups. The one or more signals detected may be optical signals, electrical signals or mechanical signals. Any suitable detector may be used including the example detectors described elsewhere herein.

The detection of one or more signals indicative of the labeled functional groups may be used to determine a nucleic acid sequence of the template nucleic acid molecule. For example, in some cases, the one or more signals indicative of the labeled functional group may be a fluorescent signal and may be detected by a fluorescence detector.

The labeled functional group may be subjected to conditions sufficient to convert the labeled functional group or any unreacted functional groups to a moiety that is substantially unreactive with the labeling reagent. In some examples, such conditions include modifying the nucleotide analog such that it obtains a structure to that of an incorporated naturally occurring nucleotide. For example, modification of the nucleotide analog may include converting its backbone structure to include natural phosphate linkages which may be substantially unreactive to the labeling reagent. In some examples, the functional group or any unreacted functional groups may be converted to a different functional group that is substantially unreactive with the labeling reagent used in the labeling reaction.

In an example, the conversion involves cleaving a phosphate to sulfur bond. The conversion may comprise converting phosphorothioate nucleic acid analogs to naturally occurring nucleotides (e.g., dNTPs). In some cases, the conversion may comprise converting phosphorothioate linkages to natural phosphate linkages. Alternatively, in some examples, the conversion may comprise converting phosphorothioate nucleic acid analogs to a modified analog that is unreactive with a label. The modified analog may be a non-naturally occurring nucleotide analog.

In another example, the conversion may involve cleaving a phosphate to selenium bond. The conversion may comprise converting phosphoroselenoate nucleic acids analogs to natural phosphate linkages. The conversion may comprise converting phosphoroselenoate nucleic acid analogs to naturally occurring nucleotides (e.g., dNTPs). Alternatively, in some examples, the conversion may comprise converting phosphoroselenoate nucleic acid analogs to a modified analog that is unreactive with a label. The modified analog may be a non-naturally occurring nucleotide analog.

In another example, the conversion may involve cleaving a linker between the label and the nucleotide analog. Cleaving the linker may convert the nucleotide analog to a moiety that is or remains substantially unreactive with the labeling reagent. In some examples, the nucleotide analog is also substantially unreactive with the labeling reagent prior to cleavage of the linker. In some examples, a part of the linker may be left on the nucleotide analog after cleaving the linker.

The conversion of the labeled functional group may comprise contacting the labeled functional group with a metal ion. The metal ion can be any suitable metal ion, including silver, mercury or lead.

The conversion of the labeled functional group may comprise contacting the labeled functional group with an oxidant. In some cases, the oxidant may be any suitable oxidant, including iodine, potassium peroxymonosulfate (oxone) or iodosobezoate.

The conversion of the labeled functional group may comprise contacting the labeled functional group with the conjugate base of an oxime (i.e., an oximate). In some cases, an oxime may be any suitable oxime, including 2-pyridine aldoxime, 4-pyridine aldoxime, obidoxime, HI 6, HLö 7, E-2-nitrobenzaldoxime or E-4-nitrobenzldoxime.

The conversion of the labeled functional group may comprise conducting a desulfurization reaction. The desulfurization reaction may include one or more of alkylation, contact of the labeled functional group with an oxidant and contacting the labeled functional group with an oxime.

In some cases, the nucleotide analog may comprise a disulfide bond coupling a label to the labeled functional group. For example, a sulfur-containing functional group may comprise a sulfur moiety that participates in disulfide exchange with a reactive moiety comprising a label, such that the label is linked to the functional group via a disulfide bond. The disulfide bond can be subjected to a desulfurization reaction that comprises subjecting the disulfide bond to conditions sufficient to reduce the disulfide bond. In some cases, this may result in generating a modified labeled functional group or regenerate the original sulfur-containing functional group. Any suitable reducing agent may be used, with examples that include Tris(2-carboxyethyl phosphine (TCEP), tris(hydroxypropyl)phosphine (THP) and dithiothreitol (DTT). In some cases, the resulting moiety comprising sulfur may be contacted with an oxidant. Any suitable oxidant may be used, including examples described elsewhere herein. Non-limiting examples of oxidants include iodine, potassium peroxymonosulfate (oxone) and iodosobenzoate.

Alternatively, in some cases, the nucleotide analog may comprise a diselenide bond coupling a label to the labeled functional group. For example, a selenium-containing functional group may comprise a selenium moiety that participates in diselenide exchange with a reactive moiety comprising a label, such that the label is linked to the functional group via a diselenide bond. The diselenide bond can be subjected to a deselenization reaction that comprises subjecting the diselenide bond to conditions sufficient to reduce the diselenide bond. In some cases, this may result in generating a modified labeled functional group or regenerate the original selenium-containing functional group. Any suitable reducing agent may be used, with examples that include Tris(2-carboxyethyl phosphine (TCEP), tris(hydroxypropyl) phosphine (THP) and dithiothreitol (DTT). In some cases, the resulting moiety comprising selenium may be contacted with an oxidant. Any suitable oxidant may be used, including examples described elsewhere herein. Non-limiting examples of oxidants include iodine, potassium peroxymonosulfate (oxone) and iodosobenzoate.

The conversion of the labeled functional group may be performed at a pH of about 3 to about 14. In some examples, the conversion of the labeled functional group may be performed at a pH of about 6 to about 11.5. In some examples, the conversion of the labeled functional group may be performed at a pH of at least about 3, at least about 3.5, at least about 4, at least about 4.5, at least about 5.0, at least about 5.5, at least about 6, at least about 6.5, at least about 7, at least about 7.5, at least about 8, at least about 8.5, at least about 9, at least about 9.5, at least about 10, at least about 10.5, at least about 11, at least about 11.5, at least about 12.0, at least about 12.5, at least about 13.0, at least about 13.5 or more. In some examples, the conversion of the labeled functional group may be performed at a pH of at most about 13.5, at most about 13.0, at most about 12.5, at most about 12, at most about 11.5, at most about 11, at most about 10.5, at most about 10, at most about 9.5, at most about 9, at most about 8.5, at most about 8, at most about 7.5, at most about 7, at most about 6.5, at most about 6.0, at most about 5.5, at most about 5.0, at most about 4.5, at most about 4.0, at most about 3.5, at most about 3.0 or less. In some examples, the conversion of the labeled functional group may be performed at a pH of about 6 to about 6.5, about 6 to about 7, about 6 to about 7.5, about 6 to about 8, about 6 to about 8.5, about 6 to about 9, about 6 to about 9.5, about 6 to about 10, about 6 to about 10.5, about 6 to about 11, about 6 to about 11.5, about 6.5 to about 7, about 6.5 to about 7.5, about 6.5 to about 8, about 6.5 to about 8.5, about 6.5 to about 9, about 6.5 to about 9.5, about 6.5 to about 10, about 6.5 to about 10.5, about 6.5 to about 11, about 6.5 to about 11.5, about 7 to about 7.5, about 7 to about 8, about 7 to about 8.5, about 7 to about 9, about 7 to about 9.5, about 7 to about 10, about 7 to about 10.5, about 7 to about 11, about 7 to about 11.5, about 7.5 to about 8, about 7.5 to about 8.5, about 7.5 to about 9, about 7.5 to about 9.5, about 7.5 to about 10, about 7.5 to about 10.5, about 7.5 to about 11, about 7.5 to about 11.5, about 8 to about 8.5, about 8 to about 9, about 8 to about 9.5, about 8 to about 10, about 8 to about 10.5, about 8 to about 11, about 8 to about 11.5, about 8.5 to about 9, about 8.5 to about 9.5, about 8.5 to about 10, about 8.5 to about 10.5, about 8.5 to about 11, about 8.5 to about 11.5, about 9 to about 9.5, about 9 to about 10, about 9 to about 10.5, about 9 to about 11, about 9 to about 11.5, about 9.5 to about 10, about 9.5 to about 10.5, about 9.5 to about 11, about 9.5 to about 11.5, about 10 to about 10.5, about 10 to about 11, about 10 to about 11.5, about 10.5 to about 11, about 10.5 to about 11.5, or about 11 to about 11.5. In some examples, the conversion of the labeled functional group may be performed at a pH of about 6, about 6.5, about 7, about 7.5, about 8, about 8.5, about 9, about 9.5, about 10, about 10.5, about 11, or about 11.5.

The conversion of the labeled functional group may be performed at a temperature of about 30° C. to about 70° C. In some examples, the conversion of the labeled functional group may be performed at a temperature of at least about 30° C., at least about 35° C., at least about 40° C., at least about 45° C., at least about 50° C., at least about 55° C., at least about 60° C., at least about 65° C., at least about 70° C. or higher. In some examples, the conversion of the labeled functional group may be performed at a temperature of at most about 70° C., at most about 65° C., at most about 60° C., at most about 55° C., at most about 50° C., at most about 45° C., at most about 40° C., at most about 35° C., at most about 30° C. or less. In some cases, the conversion of the labeled functional group may be performed at a temperature of about 45° C. to about 56° C. In some cases, the conversion of the labeled functional group may be performed at a temperature of at least about 45° C. In some cases, the conversion of the labeled functional group may be performed at a temperature of at most about 56° C. In some examples, the conversion of the labeled functional group may be performed at a temperature of about 30° C. to about 35° C., about 30° C. to about 40° C., about 30° C. to about 45° C., about 30° C. to about 50° C., about 30° C. to about 55° C., about 30° C. to about 60° C., about 30° C. to about 65° C., about 30° C. to about 70° C., about 35° C. to about 40° C., about 35° C. to about 45° C., about 35° C. to about 50° C., about 35° C. to about 55° C., about 35° C. to about 60° C., about 35° C. to about 65° C., about 35° C. to about 70° C., about 40° C. to about 45° C., about 40° C. to about 50° C., about 40° C. to about 55° C., about 40° C. to about 60° C., about 40° C. to about 65° C., about 40° C. to about 70° C., about 45° C. to about 50° C., about 45° C. to about 55° C., about 45° C. to about 60° C., about 45° C. to about 65° C., about 45° C. to about 70° C., about 50° C. to about 55° C., about 50° C. to about 60° C., about 50° C. to about 65° C., about 50° C. to about 70° C., about 55° C. to about 60° C., about 55° C. to about 65° C., about 55° C. to about 70° C., about 60° C. to about 65° C., about 60° C. to about 70° C., or about 65° C. to about 70° C. In some examples, the conversion of the labeled functional group may be performed at a temperature of about 30° C., about 35° C., about 40° C., about 45° C., about 50° C., about 55° C., about 60° C., about 65° C., or about 70° C.

The functional group in the nucleotide analogs may be undetectable. For example, absent a label, the functional group may not detectable by a method capable of detecting an associated label. After the reactions to label the functional group, it may become a detectable moiety. After detection, the labeled functional group may be subjected to a reaction that removes the functional group and may result in a moiety that is undetectable and/or unreactive with the label.

The sequencing method may further comprise repeating one or more parts of the method. The repeats of the reaction may be performed at least once using an additional plurality of free nucleotide analogs having an individual free nucleotide analog absent from the plurality of free nucleotide analogs. For example, if the first reaction was performed using thymidine nucleotide analogs, the repeat reactions may be performed without using thymidine nucleotide analogs in the reaction and may contain cytosine nucleotide analogs, adenosine nucleotide analogs or guanine nucleotide analogs. During additional cycles of primer extension reactions, incorporated nucleotide analogs can be labeled, detected and/or removed. This process can be repeated for each nucleotide analog in a set of nucleotide analogs (e.g., e.g., nucleotide analogs comprising A, T, C and G bases) and application of the entire set can also be repeated until at least a part of the template nucleic acid is sequenced.

Various example sequencing schemes are described below. In an example, a sequencing method with fluorescence detection may be used to detect the sequence of a template nucleic acid in a series of primer extension reactions with nucleotide analogs. The template nucleic acid may be immobilized on a support, such as on an example support described elsewhere herein. For instance, the support may be a magnetic bead. The template nucleic acid may be able to attach to the immobilized support molecule using adaptors.

Regardless of coupling to a support, the template nucleic acid molecule may be contacted with a primer capable of hybridizing to the template nucleic acid. The reaction mixture may also contain nucleotide analogs and a polymerizing enzyme, such as a polymerase. In some cases, the reaction mixture may comprise only one type of nucleotide analog.

In this example, the nucleic acid analogs used are alpha-thio-deoxynucleotide triphosphate (α-S-dNTP). Other nucleotide analogs may be used in different examples. α-S-dNTPs have sulfur as their functional group. The sulfur functional group containing nucleic acids may be incorporated in to the primer as a growing nucleic acid strand in the primer extension reaction with the help of a polymerase. The polymerase may be any suitable polymerase, described elsewhere herein. In this example, the nucleotide analog added for a first primer extension is alpha-thio-dTTP (α-S-dTTP) or 2'-Deoxythymidine-5'-O-1-Thiotriphosphates. α-S-dTTP may get incorporated in to the growing nucleic acid strand based on the complementarity with the template nucleic acid. FIG. 1 (panel A) shows α-S-dTTPs. The primer extension reaction may incorporate multiple α-S-dTTPs that hybridize with a homopolymer region on the nucleic acid template having consecutive adenine residues. In other examples, just one adenine base may be present on the template nucleic acid molecule at a given position, leading to the incorporation of one α-S-dTTP analog.

Following the incorporation of the α-S-dTTP, a wash cycle may be used to remove any unattached nucleotide analogs or primers. The wash buffers may be any suitable wash buffers including examples described elsewhere herein.

The nucleotide analog incorporation in the sequencing reaction, may be followed the reaction of the incorporated nucleotide analog with a labeling reagent which comprises a label as shown in FIG. 1 (panel B). The label in this example may be a labeling reagent specific for the sulfur containing nucleotide analogs. The reaction for example, as shown in FIG. 1 (panel B), may be an alkylation reaction. Fluorescent alkylating reagents may be used to label the sulfur containing functional group. For instance, Atto-647N-iodoacetamide is used in this example wherein Atto-647N is the label.

Following the attachment of the label, a wash cycle may be performed to remove any unattached labels. A detector may then be used to detect a signal indicative of the nucleotide analog (and, thus, its incorporation) (e.g., fluorescence) of the label. In this example, the label Atto-647N is a detectable label. The level of fluorescence detected corresponds to the number of nucleotide analogs incorporated in to the growing nucleic acid strand. For example in this example, fluorescence due to the incorporation of α-S-dTTPs and the attached Atto-647N dye may be used to detect that a nucleotide analog was incorporated in to the growing nucleic acid strand. Higher order signals can indicate the presence of a homopolymer.

The sequencing reaction may then include removing the labeled functional group from the nucleotide analog as shown in FIG. 1 (panel C). This may be achieved by subjecting the labeled functional group to conditions sufficient to convert the labeled functional group to a moiety that is substantially unreactive with the labeling reagent. In this example, this may involve reaction of the labeled functional group with an oximate.

In this example, the reaction of the growing nucleic acid with an oximate removes the sulfur containing functional group and converts the incorporated nucleotide analog into its natural state that may be substantially or completely unreactive with the label described above.

These reactions may then be repeated for other nucleotide analogs. For instance, in this example, they may be repeated with α-S-dATPs in the primer extension reaction. The previously detected nucleotide analogs have now been converted to natural phosphate linkages and are thus unreactive to the alkylating fluorescence reagent Atto-647N. With the new primer extension reaction a α-S-dATP(s) may be incorporated in to the growing nucleic acid strand and detection of fluorescence may be used to detect the sequence of the template nucleic acid. These reactions may then be repeated using α-S-dCTPs followed by α-S-dGTPs or repeating the 4 different α-S-dNTPs (α-S-dATPs, α-S-dTTPs, α-S-dCTPs, α-S-dGTPs) until at least a part of the template nucleic acid is sequenced. The addition of one type of nucleotide analog (in this case, thymidine analogs) followed by other type of analogs in different reactions may help reduce the chances of context dependent errors in the sequencing reactions.

In another example, a sequencing method with fluorescence detection may be used to detect the sequence of a template nucleic acid in a series of primer extension reactions with nucleotide analogs. The template nucleic acid may be immobilized on a support, such as on an example support described elsewhere herein. For instance, the support may be a magnetic bead. The template nucleic acid may be able to attach to the immobilized support molecule using adaptors.

Regardless of coupling to a support, the template nucleic acid molecule may be contacted with a primer capable of hybridizing to the template nucleic acid. The reaction mixture may also contain nucleotide analogs and a polymerizing enzyme, such as a polymerase. In some cases, the reaction mixture comprises only one type of nucleotide analog.

Figure 2:
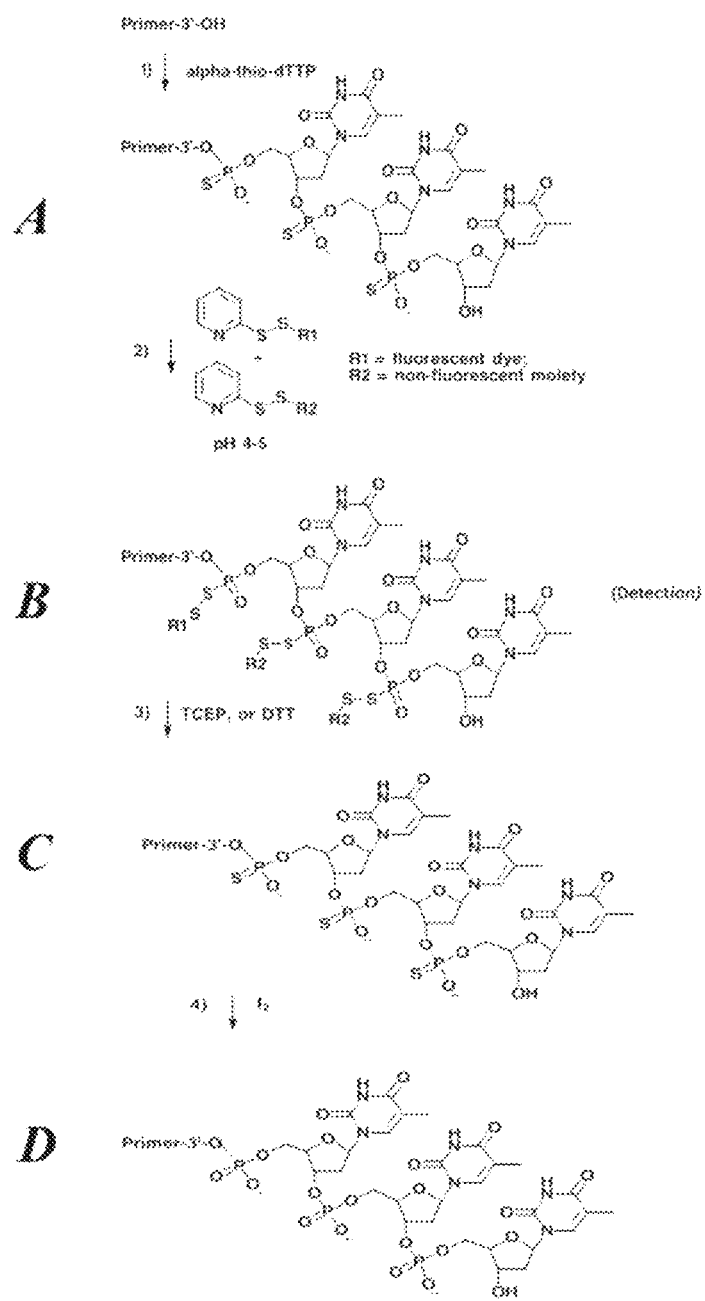
FIG. 2 shows an example sequencing reaction scheme using reducing agents.

In this example, the nucleic acid analogs used are α-S-dNTP. Other nucleotide analogs may be used in other examples. α-S-dNTPs have sulfur as their functional group. The sulfur functional group containing nucleic acids may be incorporated in to the primer as a growing nucleic acid strand in the primer extension reaction with the help of a polymerase. The polymerase may be any suitable polymerase, described elsewhere herein. In this example, the nucleotide analog added for a first primer extension is alpha-thio-dTTP (α-S-dTTP) or 2'-Deoxythymidine-5'-O-1-Thiotriphosphates. α-S-dTTP may get incorporated in to the growing nucleic acid strand based on the complementarity with the template nucleic acid. FIG. 2 (panel A) shows α-S-dTTPs. The primer extension reaction may incorporate multiple α-S-dTTPs that hybridize to a homopolymer region on the nucleic acid template having consecutive adenine residues. In other examples, just one adenine base may be present on the template nucleic acid molecule at a given position, leading to the incorporation of one α-S-dTTP analog.

Following the incorporation of the α-S-dTTP, a wash cycle may be used to remove any unattached nucleotide analogs or primers. The wash buffers may be any suitable wash buffers including examples described elsewhere herein.

The sequencing reaction may then be continued with the reaction of the growing nucleic acid strand with a labeling reagent that may be a combination of a fluorescent dye (R1 in FIG. 2. Panel B) and a non-fluorescent moiety (R1 in FIG. 2. Panel B). The label in this example may attach to a non-fluorescent moiety specific for the sulfur containing nucleotide analogs. The reaction that leads to the attachment of the nucleic acid analog to the non-fluorescent moiety and label may for example be an alkylation reaction. Fluorescent alkylating reagents may be used to label the sulfur containing functional group. The alkylation reaction may be performed at a suitable pH (e.g., pH 4-5 in this example).

Following the attachment of the label and the non-fluorescent moiety, a wash cycle may be performed to remove any unattached labels. A detector may then be used to detect a signal indicative of the nucleotide analog (and, thus, its incorporation) (e.g., fluorescence) of the label. The level of fluorescence detected corresponds to the number of nucleotide analogs incorporated in to the growing nucleic acid strand. For example in this example, fluorescence due to the incorporation of α-S-dTTPs and the attached dye may be used to detect that a nucleotide analog was attached to the growing nucleic acid strand. Higher order signals can indicate the presence of a homopolymer.

The sequencing reaction may then continue with the removal of the labeled functional group from the nucleotide analog as shown in FIG. 2 (panels B and C). This may be achieved by subjecting the labeled functional group to conditions sufficient to convert the labeled functional group to a moiety that is substantially unreactive with the labeling reagent. In some cases, the disulfide bond coupling the label to sulfur functional group may be reacted with conditions sufficient to reduce the disulfide bond, and generating a modified sulfur functional group. In this example, the reducing agents used are Tris(2-carboxyethyl phosphine (TCEP), tris(hydroxypropyl)phosphine (THP) or dithiothreitol (DTT).

In this example, the growing nucleic acid strand is reacted with reducing agents and then treated with oxidants such as Iodine leading to a desulfurization reaction, as shown in FIG. 2 (panel D). The sulfur containing functional group, in this example, may be replaced with a natural phosphate functional group that may be essentially unreactive with the alkylating fluorescent reagents.

In this example, the reaction of the growing nucleic acid with one or more metal ions removes the sulfur containing functional group and converts the incorporated nucleotide analog into its natural state that may be substantially or completely unreactive with the label described above.

These reactions may then be repeated for other nucleotide analogs. For instance, in this example, they may be repeated with α-S-dATPs in the primer extension reaction. The previously detected nucleotide analogs have now been converted to natural phosphate linkages and are thus unreactive to the alkylating fluorescence reagent. With the new primer extension reaction a α-S-dATP(s) may be incorporated in to the growing nucleic acid strand and detection of fluorescence may be used to detect the sequence of the template nucleic acid. These reactions may then be repeated using α-S-dCTPs followed by α-S-dGTPs or repeating the 4 different α-S-dNTPs (α-S-dATPs, α-S-dTTPs, α-S-dCTPs, α-S-dGTPs) until at least a part of the template nucleic acid is sequenced. The addition of one type of nucleotide analog (in this example, thymidine analogs) followed by other type of analogs in different reactions may help reduce the chances of context dependent errors in the sequencing reactions.

In yet another example, a sequencing method with fluorescence detection may be used to detect the sequence of a template nucleic acid in a series of primer extension reactions with nucleotide analogs. The template nucleic acid may be immobilized on a support, such as on an example support described elsewhere herein. For instance, the support may be a magnetic bead. The template nucleic acid may be able to attach to the immobilized support molecule using adaptors.

Regardless of coupling to a support, the template nucleic acid molecule may be contacted with a primer capable of hybridizing to the template nucleic acid. The reaction mixture may also contain nucleotide analogs and a polymerizing enzyme, such as a polymerase. In some cases, the reaction mixture comprises only one type of nucleotide analog.

Figure 3:
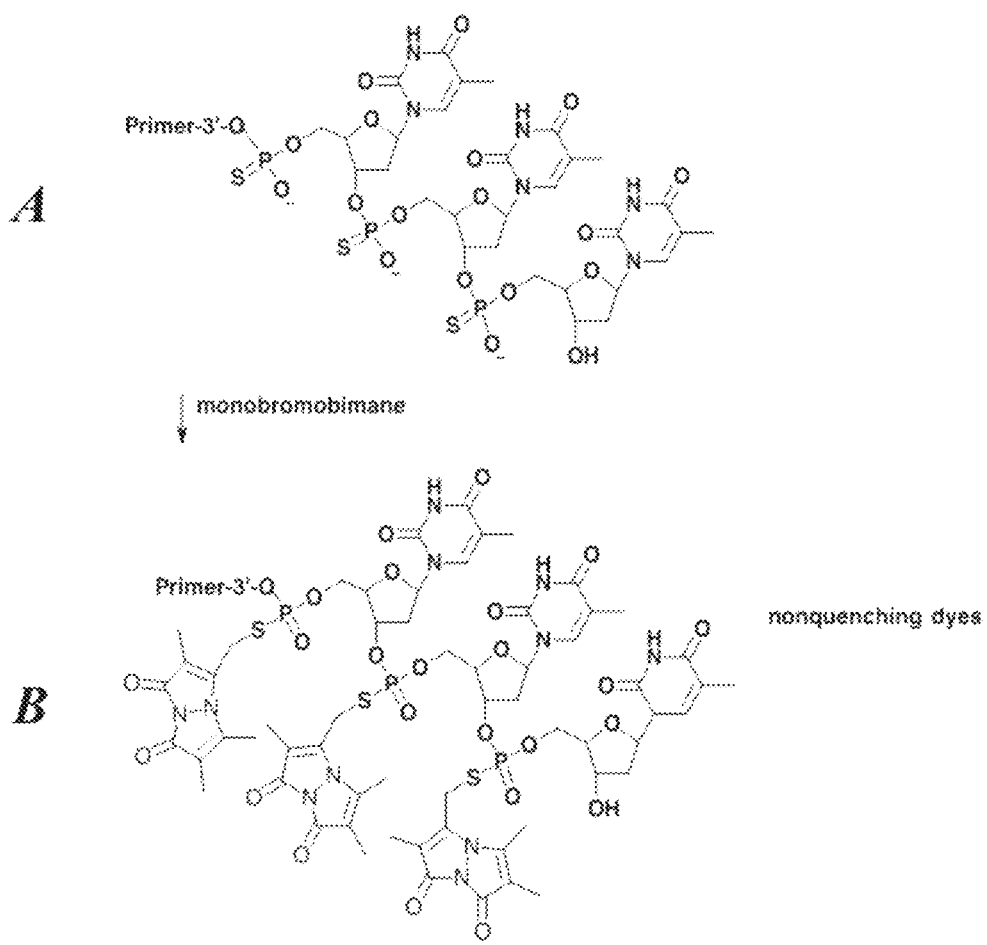
FIG. 3 shows an example sequencing reaction scheme using non-quencher dyes.

In this example, the nucleic acid analogs used are α-S-dNTPs. Other nucleotide analogs may be used in different cases. The sulfur functional group containing nucleic acids may be incorporated in to the primer as a growing nucleic acid strand in the primer extension reaction with the help of a polymerase. The polymerase may be any suitable polymerase, described elsewhere herein. In this example, the nucleotide analog added for a first primer extension is α-S-dTTP or 2'-Deoxythymidine-5'-O-1-Thiotriphosphates. α-S-dTTP may get incorporated in to the growing nucleic acid strand based on the complementarity with the template nucleic acid. FIG. 3 (panel A) shows α-S-dTTPs. The primer extension reaction may incorporate multiple α-S-dTTPs that hybridize to a homopolymer region on the nucleic acid template having consecutive adenine residues. In other examples, just one adenine base may be present on the template nucleic acid molecule at a given position, leading to the incorporation of one α-S-dTTP analog.

Following the incorporation of the α-S-dTTP, a wash cycle may be used to remove any unattached nucleotide analogs or primers. The wash buffers may be any suitable wash buffers including examples described elsewhere herein.

The sequencing reaction may be continued with the reaction of the incorporated nucleotide analog with a labeling reagent which comprises a label as shown in FIG. 3 (panel A). The labeling reagent in this example may be a reagent specific for the sulfur containing nucleotide analogs. The reaction for example, as shown in FIG. 3 (panel B), may be an alkylation reaction. In some cases, where the fluorescent dyes do not quench when attached to adjacent bases, just one reagent may be used for the alkylation reaction. Fluorescent alkylating reagents such as monobromobimane may be used as labeling reagents to label the sulfur containing functional group.

Following the attachment of the label (monobromobimane in this example), a wash cycle may be performed to remove any unattached fluorescent labels. A detector may then be used to detect a signal indicative of the nucleotide analog (and, thus, its incorporation) (e.g., fluorescence) of the label. In this example, the label monobromobimane is a detectable label. The level of fluorescence detected corresponds to the number of nucleotide analogs incorporated in to the growing nucleic acid strand. In this example, fluorescence due to the incorporation of α-S-dTTP(s) and the attached monobromobimane dye may be used to detect that a nucleotide analog was attached to the growing nucleic acid strand. Higher order signals can indicate the presence of a homopolymer.

The sequencing reaction may then continue with the removal of the labeled functional group from the nucleotide analog. This may be achieved by subjecting the labeled functional group to conditions sufficient to convert the labeled functional group to a moiety that is substantially unreactive with the labeling reagent. In this example, this may involve reaction of the labeled functional group with one or more metal ions.

In this example, the reaction of the growing nucleic acid with one or more metal ions removes the sulfur containing functional group and converts the incorporated nucleotide analog into its natural state that may be substantially or completely unreactive with the label described above.

These reactions may then be repeated for other nucleotide analogs. For instance, in this example, they may be repeated with α-S-dATPs in the primer extension reaction. The previously detected nucleotide analogs have now been converted to natural phosphate linkages and are thus unreactive to the alkylating fluorescence reagent monobromobimane. With the new primer extension reaction a α-S-dATP may be incorporated in to the growing nucleic acid strand and detection of fluorescence may be used to detect the sequence of the template nucleic acid. These reactions may then be repeated using α-S-dCTPs followed by α-S-dGTPs or repeating the 4 different α-S-dNTPs (α-S-dATPs, α-S-dTTPs, α-S-dCTPs, α-S-dGTPs) until at least a part of the template nucleic acid is sequenced. The addition of one type of nucleotide analog (in this case, thymidine analogs) followed by other type of analogs in different reactions may help reduce the chances of context dependent errors in the sequencing reactions.

In yet another example, a sequencing method with fluorescence detection may be used to detect the sequence of a template nucleic acid in a series of primer extension reactions with nucleotide analogs. The template nucleic acid may be immobilized on a support, such as on an example support described elsewhere herein. For instance, the support may be a magnetic bead. The template nucleic acid may be able to attach to the immobilized support molecule using adaptors.

Regardless of coupling to a support, the template nucleic acid molecule may be contacted with a primer capable of hybridizing to the template nucleic acid. The reaction mixture may also contain nucleotide analogs and a polymerizing enzyme, such as a polymerase. In some cases, the reaction mixture comprises only one type of nucleotide analog.

Figure 8:
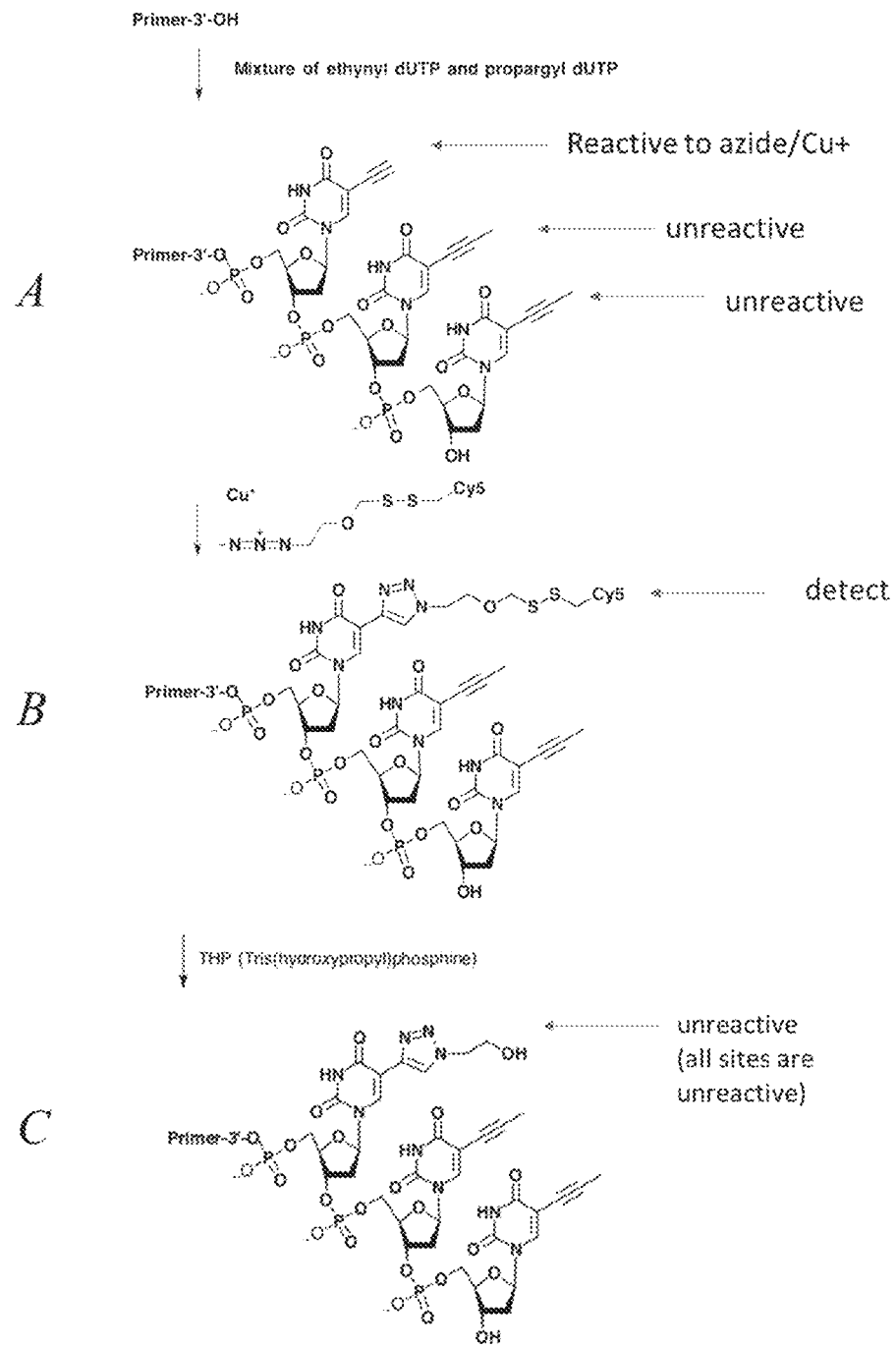
FIG. 8 shows an example sequencing reaction scheme using enzymatic incorporation of a mixture of internal and terminal alkyne substrates that are subsequently labeled with a dye-azide in a copper(I) catalyzed reaction.

In this example, the nucleic acid analogs used are a mixture of ethynyl nucleotide analogs and 1-propynyl nucleotide analogs. Other nucleotide analogs may be used in different examples. The ethynyl functional group containing nucleic acids and 1-propynyl functional group containing nucleic acids may be incorporated in to the primer as a growing nucleic acid strand in the primer extension reaction with the help of a polymerase. The polymerase may be any suitable polymerase, described elsewhere herein. In this example, the nucleotide analog randomly added for a first primer extension is ethynyl-dUTP followed by two additions of the 1-propynyl dUTPs. Such nucleic acids may get incorporated in to the growing nucleic acid strand based on the complementarity with the template nucleic acid. The ratio of ethynyl dUTP to propynyl dUTP incorporation used may be proportional to their concentrations in solution and independent of sequence context. The similarity between the ethynyl and the propynyl groups may lead to minimal or no discrimination by the polymerase enzyme during their incorporation in to the growing strand. Other nucleotide analog pairs with similar structures may be used in other examples. In this example, the 1-propynyl analog may not be reactive in the subsequent copper click reaction with azide since it is not a terminal alkyne. The use of unreactive analogs may allow the subsequent labeling with dyes, such as Cy5, that show proximity quenching, by spacing out the dyes. A similar result may be achieved by using an ethynyl analog alone in the primer extension step, followed by a copper click reaction with a mixture of CY5-azide and 3-azido-1- propanol (a 'bright" and "dark" label, respectively). FIG. 8 (panel A) shows incorporation of the three dUTPs (ethynyl dUTP and two 1-propynyl dUTPs). The primer extension reaction may incorporate multiple nucleotides that hybridize with a homopolymer region on the nucleic acid template having consecutive adenine residues. In other examples, just one adenine base may be present on the template nucleic acid molecule at a given position, leading to the incorporation of one ethynyl dUTP or one propynyl analog.

Following the incorporation of the ethynyl dUTP and 1-propynyl nucleotide analogs, a wash cycle may be used to remove any unattached nucleotide analogs or primers. The wash buffers may be any suitable wash buffers including examples described elsewhere herein.

The nucleotide analog incorporation in the sequencing reaction may be followed by the reaction of the incorporated nucleotide analog with a labeling reagent as shown in FIG. 8 (panel B). The label in this example may be a label specific for the ethynyl containing nucleotide analogs. The reaction for example, as shown in FIG. 8 (panel B), may be a click reaction that comprises using copper. Fluorescent reagents may be used to label the ethynyl containing functional group. For instance, Cy5-azide is used in this example. The product of the click reaction may be a triazole connecting the nucleotide with the label, in this example, Cy5. In this example, the 1-propynyl containing nucleic acids are unreactive to the Cy5-azide label in the copper click reaction. The 1-propynyl dUTP is incorporated as a partner with the ethynyl dUTP. In other examples, natural dNTPs may be used as a partner with the ethynyl dNTPs.

Following the attachment of the label, a wash cycle may be performed to remove any unattached labels. A detector may then be used to detect a signal indicative of the nucleotide analog (and, thus, its incorporation) (e.g., fluorescence) of the label. In this example, the label Cy5-azide is a detectable label. The level of fluorescence detected corresponds to the number of nucleotide analogs incorporated in to the growing nucleic acid strand. For example in this example, fluorescence due to the incorporation of a ethynyl dUTP and the attached Cy5-azide dye may be used to detect that a nucleotide analog was incorporated in to the growing nucleic acid strand. Higher order signals can indicate the presence of a homopolymer.

The sequencing reaction may then include removing the labeled functional group from the nucleotide analog as shown in FIG. 8 (panel C). This may be achieved by subjecting the labeled functional group to conditions sufficient to convert the labeled functional group to a moiety that is substantially unreactive with the labeling reagent. In this example, this may involve reaction of the labeled functional group with a reducing agent, THP. The labeled function group from the nucleotide analog may be substantially unreactive with the labeling reagent prior to such reaction with the reducing agent.

In this example, the reaction of the growing nucleic acid with a reducing agent can cleave the label attached to the nucleotide analog. A part of the linker may be left on the nucleotide analog. This cleavage may lead to the conversion of the incorporated nucleotide analog into a nucleotide analog that may be substantially unreactive with the labeling reagent. The incorporated nucleotide analog may be substantially unreactive with the labeling reagent prior to such cleavage.

These reactions may then be repeated for other nucleotide analogs. For instance, these reactions may be repeated with a mixture of 7-ethynyl-7-deaza-dATP and 7-(1-propynyl)-7-deaza-dATP in the primer extension reaction. The incorporated propynyl containing nucleotides may be unreactive to the fluorescence reagent Cy5-azide. With the new primer extension reaction, 7-ethynyl-7-deaza-dATP(s) may be incorporated in to the growing nucleic acid strand, reacted with Cy-5-azide, and detection of fluorescence may be used to detect the sequence of the template nucleic acid. These reactions may then be repeated using 5-ethynyl-dCTPs with 5-(1-propynyl)-dCTP, followed by 7-ethynyl-7-deaza-dGTPs with 7-(1-propynyl)-7-dGTP, or repeating the 4 different ethynyl/propynyl dNTPs (ethynyl/propynyl dATPs, ethynyl/propynyl dUTPs, ethynyl/propynyl dCTPs, ethynyl/propynyl dGTPs) until at least a part of the template nucleic acid is sequenced.

In yet another example, a sequencing method with fluorescence detection may be used to detect the sequence of a template nucleic acid in a series of primer extension reactions with nucleotide analogs. The template nucleic acid may be immobilized on a support, such as on an example support described elsewhere herein. For instance, the support may be a magnetic bead. The template nucleic acid may be able to attach to the immobilized support molecule using adaptors.

Regardless of coupling to a support, the template nucleic acid molecule may be contacted with a primer capable of hybridizing to the template nucleic acid. The reaction mixture may also contain nucleotide analogs and a polymerizing enzyme, such as a polymerase. In some cases, the reaction mixture comprises only one type of nucleotide analog.

Figure 9:
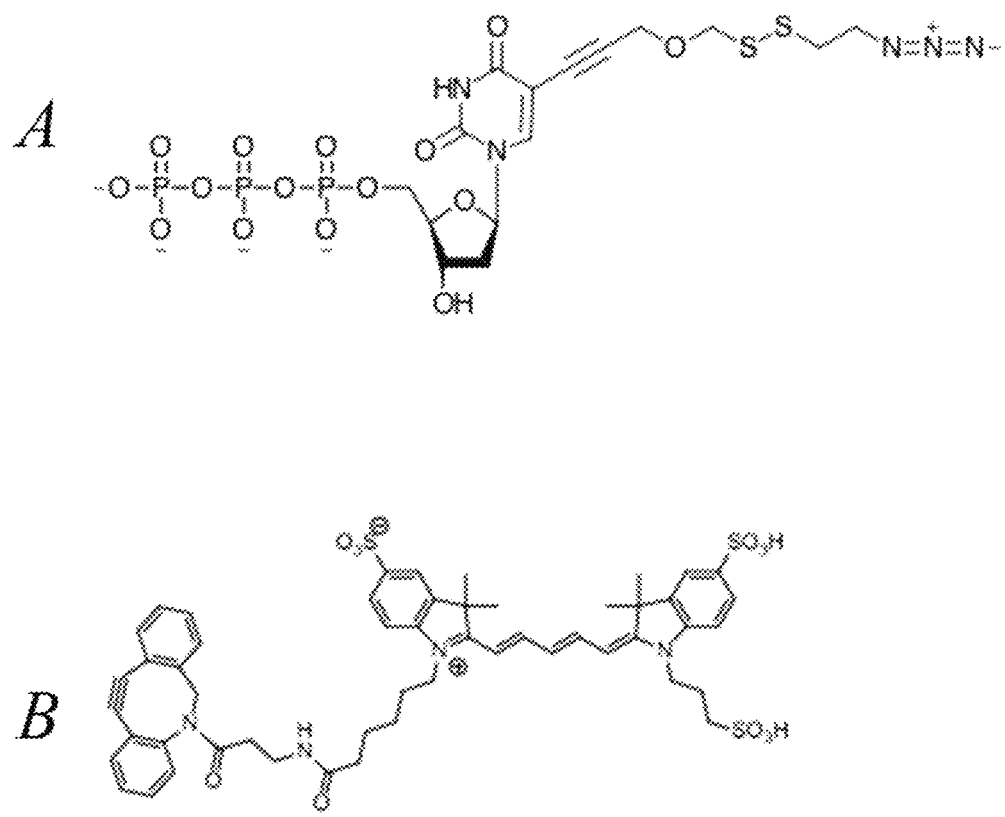
FIG. 9 shows an example of a cleavable, azide labeled nucleotide analog and an example of a dye-labeled cyclooctyne reagent (Cy5-DBCO).

In this example, the nucleic acid analogs used are cleavable azidonucleotide analogs. Other nucleotide analogs may be used in different examples. The azido functional group containing nucleic acids may be incorporated in to the primer as a growing nucleic acid strand in the primer extension reaction with the help of a polymerase. The polymerase may be any suitable polymerase, described elsewhere herein. In this example, the nucleotide analog added for a first primer extension is azido-dUTP. Such nucleic acids may get incorporated in to the growing nucleic acid strand based on the complementarity with the template nucleic acid. FIG. 9 (panel A) shows the structure of a cleavable azido dUTP. The primer extension reaction may incorporate multiple nucleotides that hybridize with a homopolymer region on the nucleic acid template having consecutive adenine residues. In other examples, just one adenine base may be present on the template nucleic acid molecule at a given position, leading to the incorporation of one azido dUTP analog.

Following the incorporation of the azido dUTP, a wash cycle may be used to remove any unattached nucleotide analogs or primers. The wash buffers may be any suitable wash buffers including examples described elsewhere herein.

The nucleotide analog incorporation in the sequencing reaction, may be followed by the reaction of the incorporated nucleotide analog with a labeling reaction (comprising a a label) as shown in FIG. 9 (panel B). The label in this example may be a label specific for the azido containing nucleotide analogs. The reaction for example, as shown in FIG. 9 (panel B), may be a click reaction that may not need copper. Fluorescent reagents may be used to label the azido containing functional group. For instance, Cy5-dibenzocyclooctyne (DBCO) is used in this example.

Following the attachment of the label, a wash cycle may be performed to remove any unattached labels (e.g., unreacted labeling reagents). A detector may then be used to detect a signal indicative of the nucleotide analog (and, thus, its incorporation) (e.g., fluorescence) of the label. In this example, the label Cy5-DBCO is a detectable label. The level of fluorescence detected corresponds to the number of nucleotide analogs incorporated in to the growing nucleic acid strand. For example in this example, fluorescence due to the incorporation of a azido dUTP and the attached Cy5-DBCO dye may be used to detect that a nucleotide analog was incorporated in to the growing nucleic acid strand. Higher order signals can indicate the presence of a homopolymer.

The sequencing reaction may then include removing the labeled functional group from the nucleotide analog. In this example, the dye may be removed by treating the labeled functional group with a reducing reagent, for example, THP, to remove the dye. The labeled functional group may be substantially unreactive with the labeling reagent prior to such reaction with the reducing reagent.

These reactions may then be repeated for other nucleotide analogs. For instance, in this example, they may be repeated with azido dATPs in the primer extension reaction. The previously detected nucleotide analogs have now been converted to triazole containing nucleotides and thus unreactive to the fluorescence reagent Cy5-DBCO. With the new primer extension reaction azido dATP(s) may be incorporated in to the growing nucleic acid strand and detection of fluorescence may be used to detect the sequence of the template nucleic acid. These reactions may then be repeated using azido dCTPs followed by azido dGTPs or repeating the 4 different azido dNTPs (azido dATPs, azido dUTPs, azido dCTPs, azido dGTPs) until at least a part of the template nucleic acid is sequenced. The addition of one type of nucleotide analog (in this case, thymidine analogs) followed by other type of analogs in different reactions may help reduce the chances of context dependent errors in the sequencing reactions.

Computer Systems

Figure 7:
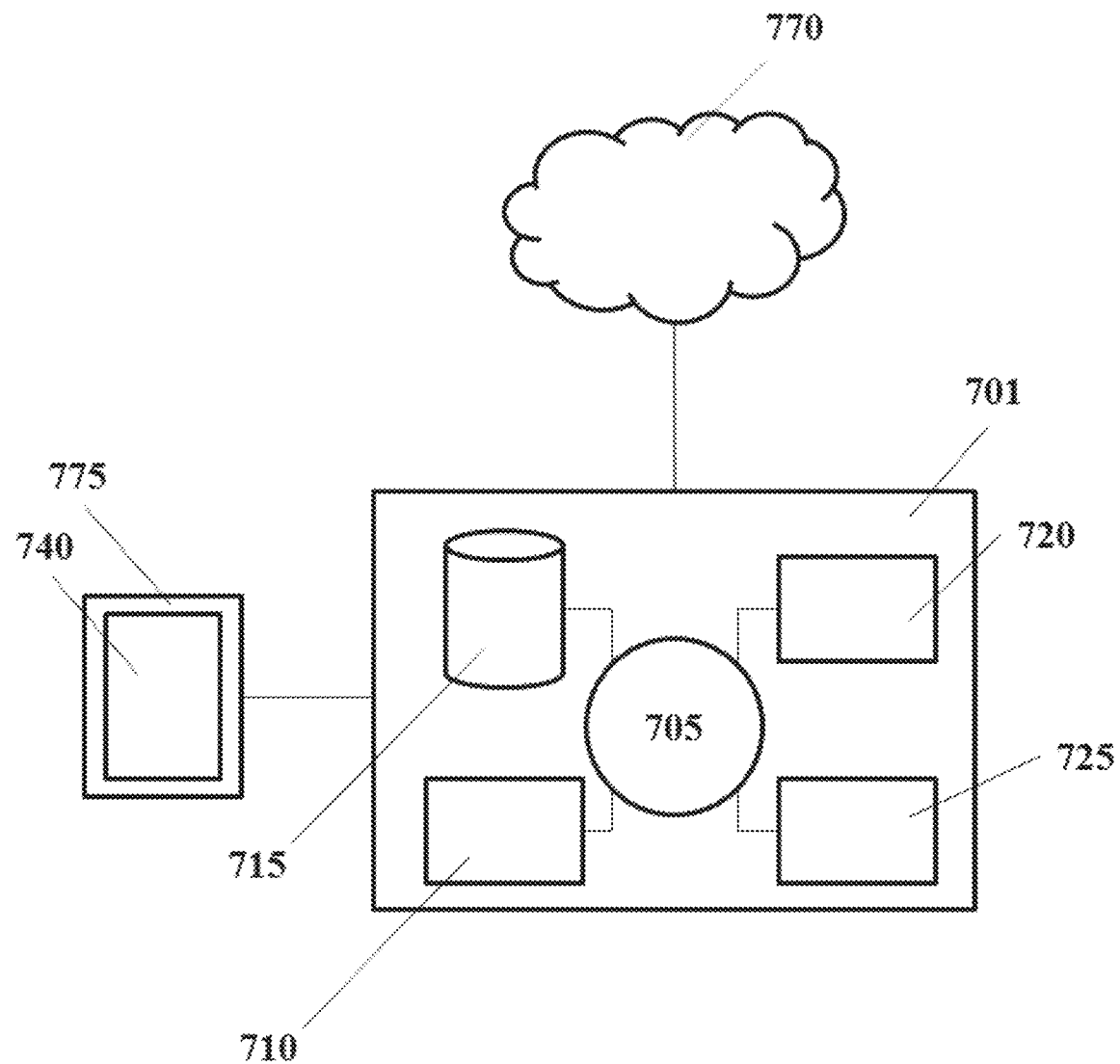
FIG. 7 shows an example computer system that is programmed or otherwise configured to implement methods provided herein.

The present disclosure provides computer systems that are programmed to implement methods of the disclosure. FIG. 7 shows a computer system 701 that is programmed or otherwise configured implement methods described herein, including methods for nucleic acid sequencing, detection of labeled nucleotides and nucleotide analogs and also configured to operate associated instrumentation. The computer system 701 can regulate various aspects of the sequencing reactions of the present disclosure, such as, for example, the addition of various reagents, the detection of the fluorescent labels, the wash cycles and other reactions.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user (e.g., computer system attached to a detector to detect the nucleotide sequence based on label detection). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, for example, results of nucleic acid sequencing experiments, information associated with nucleic acid sequencing results, raw data for label detection, duration and temperature of primer extension, duration, pH and time for the removal of functional group reaction or information about the wash cycles. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 705. The algorithm can, for example, be used to change the duration of a reaction or primer extension, time to detect the label attached to analogs, the pH and time for the functional group removal reaction or repeating the sequencing reaction for various kinds of nucleotide analogs.

EXAMPLES

Example 1

Association of a Template Nucleic Acid Molecule to a Surface

This example is directed to the immobilization of a template nucleic acid molecule to a magnetic bead and hybridization of a primer. In this example, a solution of biotinylated template (2 uL of 100 uM) and five dye-labeled primers (20 uL of 2 uM each) were combined in annealing buffer (40 uL; Tris (10 mM), EDTA (1 mM), NaCl (100 mM)). The solution was heated to 95° C. and allowed to slowly cool to room temperature. A portion of this solution (8 uL) was mixed with streptavidin-labeled magnetic beads (4 uL of Invitrogen Dynabeads™ MyOne™ Streptavidin C1, 10 mg/mL; washed and eluant removed) and 2× bead wash buffer (8 uL; 10 mM Tris, pH 7.5, 1 mM EDTA, 2 M NaCl, 0.01% Triton X-100). After washing with TET (10 mM Tris, 1 mM EDTA, 0.05% Triton X-100) solution the beads were treated with Bst DNA polymerase v.2.0 (8 uL of 8 U/uL; New England Biolabs) for five minutes. The excess enzyme was removed by washing with TET and the beads were suspended in 1×DNA polymerase buffer solution (20 mM Tris, pH 8, 10 mM NaCl, 2 mM MgC12, 0.01% Triton X-100).

The sequence of biotinylated template was as follows: /52-Bio//iSp18/ GATCGTTCGCGCACGCGACGTTCAGCGCAGCGC-GATTCGACAGCAGCGC ATTCACAGCGCGCGCAACTGAGTCGGAGACACGCAGG-GATGAGATGG (SEQ ID NO: 1) where 5 indicates the 5'-end of the oligo, 2-Bio indicates dual biotin, and iSP18 indicates a PEG spacer. Sequences of dye-labeled primers: primer 1)/56-FAM/CCATCT-CATCCCTGCGTGTCTCCGAC (SEQ ID NO: 2), primer 2)/56-FAM/ TTTTTTTTTTTGTCTCCGACTCAGTTGCGCGCGCT GTGAA (SEQ ID NO: 3), primer 3)/56-FAM/ TTTTTTTTTTTTTTTTTTTT TTTAGTTGCGCGCGCTGTGAATGCGCTGCTG (SEQ ID NO: 4), primer 4)/56-FAM/ TTTTTTTTTTTTTTTTTTTTTTTTTTTTTTT TTGCTGT-GAATGCGCTGCTGTCGAATCGCGC (SEQ ID NO: 5), and primer 5)/56-FAM/ TTTTTTTTTTTTTTTTTTTTTTTTTTTTTTTTTTTTTTT TTTTTTCGAATCGCGCTGC GCTGAACGTCGCG (SEQ ID NO: 6); where 5' indicates the 5'-end of the oligonucleotide and 6FAM/indicates a fluorescent dye attached to the oligonucleotide. The polyT portion allows separation of the oligonucleotides and extension products on capillary electrophoresis.

Example 2

Single Nucleotide Extension of a Primed Template

This example is directed to the extension of the primed template with a single nucleotide analog. In this example, magnetic beads from Example 1 were resuspended in 1× polymerase buffer (72 uL) in a PCR tube. A solution of α-S-dTTP (8 uL of 1 mM) was added to the tube and the tube incubated for 40 sec at 50° C. The enzyme reaction was stopped with the addition of 5 uL of 50 mM EDTA. The beads were washed with 2×100 uL TET and resuspended in 80 uL TET. The beads were separated into 8 tubes of 10 uL each of suspended beads. The eluant of the beads was removed and 20 uL of pH 7 Tris buffer was added to each tube. A solution of Atto647N iodoacetamide in DMF (12 mM) was prepared, and an aliquot (1 uL) of the solution was added to each tube. The reaction was stopped by washing with TET (3×200 uL) after one minute, ten minutes and 30 minutes. A solution of 95:5 formamide:10 mM EDTA (10 uL) was added to the beads. A portion of the formamide solution (1 uL) was added to 40 uL 95:5 formamide EDTA. The solutions were examined by capillary electrophoresis (ABI 3730) and the peaks identified; as shown in FIG. 4.

Figure 4:
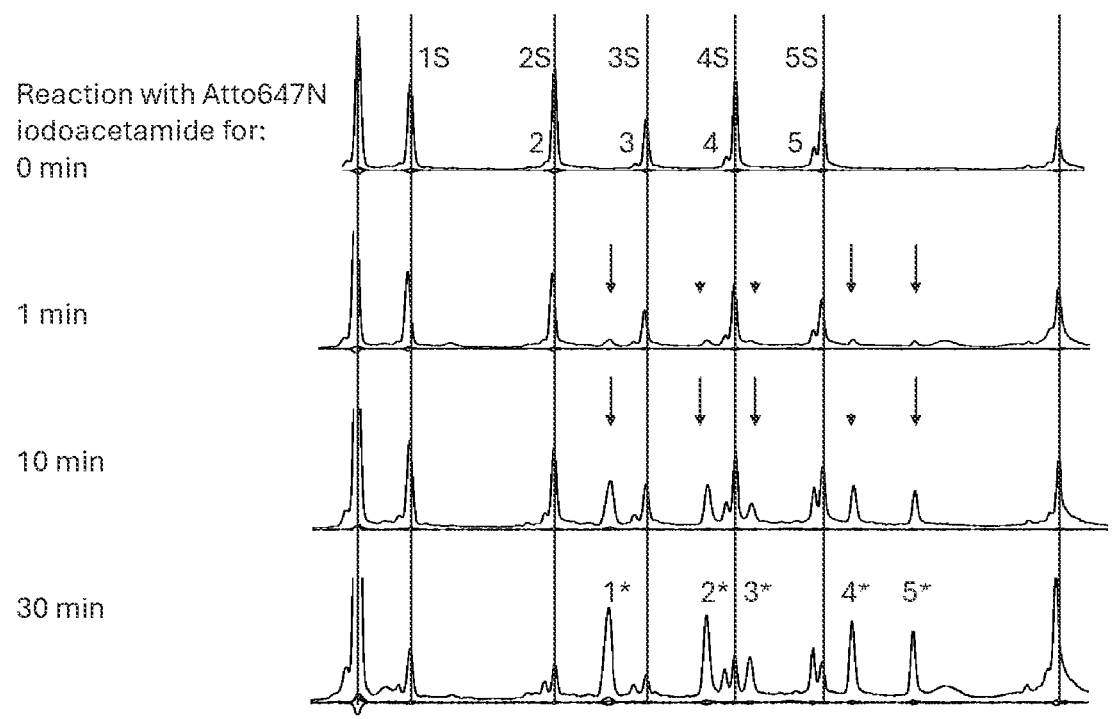
FIG. 4 shows the detection results from an example capillary electrophoresis reaction.
Figure 5A:
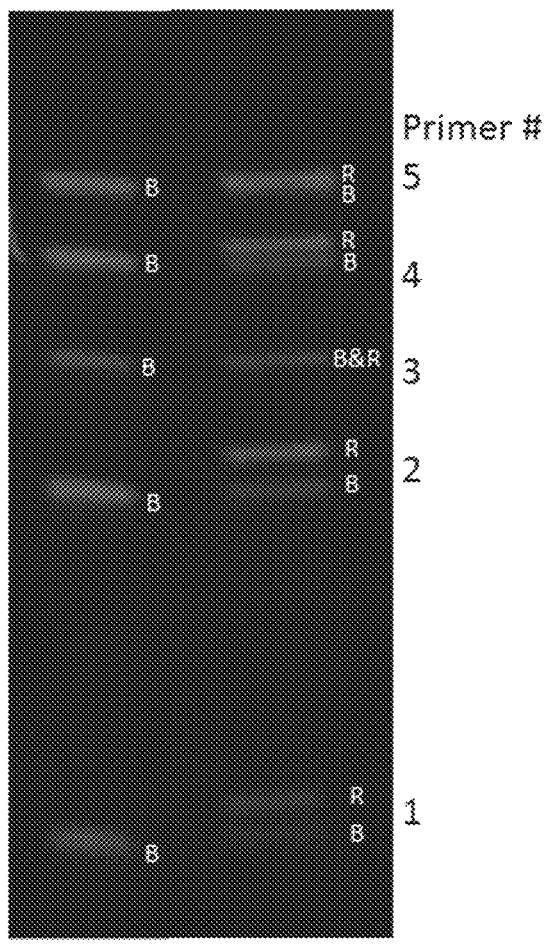
FIGS. 5A and 5B show dye labeled primer results from an example capillary electrophoresis reaction.
Figure 5B:
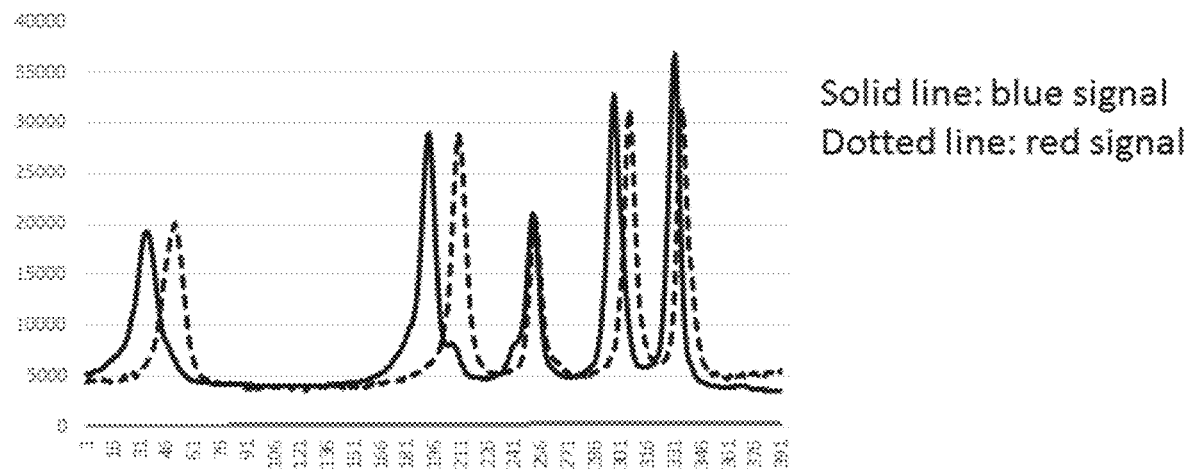

FIG. 4 shows results of a capillary electrophoresis experiment of a multiplex of five FAM-primers after incorporation of α-S-dTTP and treatment with Atto647N iodoacetamide for 0 min, 1 min, 10 min and 30 min. Peaks corresponding to the dye-labeled extension products increase over time. Peak heights appear to be independent of sequence context. Identification: Primers labeled 1S, 2S, 3S,4S and 5S are each primer (1-5) extended with a single α-S-dTTP. Primers extended with α-S-dTTP and alkylated with Atto647N-iodoacetamide are labeled 1*, 2*, 3*, 4*, 5* (and also with arrows); unextended primers are labeled 2, 3, 4, 5 (no unextended primer 1 is observed). After primer extension reactions as listed before, the Atto-647N-Iodoacetamide dye was reacted with the nucleotide analogs as explained above. As shown in FIG. 5A, five primers labeled with reporter label FAM where used for the primer extension. Lane 1 shows the reaction with just α-S-dTTP, showing a blue signal, whereas lane 2 shows the results with the α-S-dTTPs and then the Atto-647-Iodoacetamide dye attached to them thus showing a red signal. Five primers labeled with reporter label FAM (blue) and Atto647N (red) were run on an acrylamide gel and the signals were read. The band intensities were analyzed on Image J software and the results are as shown in FIG. 5B. The red peaks were proportional in height to the blue peaks, indicating context-independent labeling.

Example 3

Removal of Dye Labeled Functional Group

Figure 6:
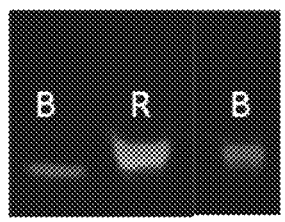
FIG. 6 shows results after an example desulfurization reaction.

In this example, a reaction was started with a primer attached to a reporter label FAM. 5'FAM-CCATCTCATCCCTGCGTGTCTCCGAC*T (SEQ ID NO: 7), (FAM-primer-aS-T) where (*) indicates a phosphorothioate linkage. The primer was annealed to its biotinylated complement: /52-Bio//iSp18/TTGCTTGCTTGCTTGCACTGAGTCGGA-GACACGCAGGGATGAGATGG (SEQ ID NO: 8). The duplex was captured on a streptavidin magnetic bead. The phosphorothioate moiety was alkylated with Atto647N-iodoactamide (0.12 mM in pH 9 CAPS buffer, RT, 15 min). The excess dye was removed with washes of 1:3 acetonitrile and 0.1 M triethylammonium acetate buffer. The dye was cleaved by heating the beads in pH 10 borate buffer with 50 mM 2-PAM (2-pyridine aldoxime methyl chloride), giving the Fam-primer-T oligonucleotide, free of dye. In FIG. 6, Lane 1 shows the capillary electrophoresis results where the blue band is the result using just the primer. Lane 2 shows a red band indicative of the primer and the fluorescent dye Atto-647N-Iodoacetamide attached to the nucleotide analog. Lane 3 shows the resulting blue band after cleavage with the borate and 2-PAM at pH of about 10.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for determining a sequence of a template nucleic acid molecule, comprising:
   (a) contacting two or more nucleotide analogs with a growing nucleic acid strand having sequence complementarity with said template nucleic acid molecule, under conditions sufficient to incorporate said two or more nucleotide analogs into said growing nucleic acid strand, wherein said nucleotide analogs comprise a modified phosphate group comprising sulfur or selenium;
   (b) reacting at least one of said modified phosphate group of said nucleotide analogs with a labeling reagent comprising a label to generate a label-S-P, label-S-S-P, or label-Se-P group on said growing nucleic acid strand;
   (c) detecting one or more signals indicative of said label; and
   (d) converting said label-S-P, label-S-S-P, or label-Se-P group to an O=P group on said growing nucleic acid strand.

2. The method of claim 1, further comprising sequencing said template nucleic acid molecule based at least in part on said one or more signals detected in (c).

3. The method of claim 1, wherein (a) comprises: contacting a plurality of nucleotides of a same canonical base, including said two or more nucleotide analogs, to said growing nucleic acid strand, under conditions sufficient to incorporate at least two nucleotides of said plurality of nucleotides, including said two or more nucleotide analogs, into said growing nucleic acid strand.

4. The method of claim 3, wherein said plurality of nucleotides of said same canonical base each comprises a modified phosphate group comprising sulfur or selenium.

5. The method of claim 3,
   wherein (a) comprises: contacting said plurality of nucleotides of said same canonical base, including said two or more nucleotide analogs each comprising a modified phosphate group comprising sulfur or selenium, to a plurality of growing nucleic acid strands, including said growing nucleic acid strand, under conditions sufficient to incorporate at least two nucleotides of said plurality of nucleotides into each of said plurality of growing nucleic acid strands, wherein said plurality of growing nucleic acid strands has sequence identity;
   wherein (b) comprises: reacting a plurality of labeling reagents, at least a subset each comprising said label, with at least a subset of modified phosphate groups incorporated in said plurality of growing nucleic acid strands, to generate label-S-P, label-S-S-P, or label-Se-P groups across said plurality of growing nucleic acid strands;
   wherein in (c): said one or more signals are indicative of said labels; and
   further comprising determining a sequence of a homopolymer region on said template nucleic acid molecule based at least in part on said one or more signals.

6. The method of claim 5, wherein in (b) at least two label-S-P, label-S-S-P, or label-Se-P groups of said label-S-P, label-S-S-P, or label-Se-P groups are generated on a same growing nucleic acid strand.

7. The method of claim 1, wherein said two or more nucleotide analogs each comprises alpha-thio-deoxynucleotide triphosphate (α-S-dNTP).

8. The method of claim 1, wherein said template nucleic acid molecule is immobilized to a support.

9. The method of claim 8, wherein said support is a bead.

10. The method of claim 8, wherein said support is a substantially planar surface.

11. The method of claim 1, wherein said labeling reagent comprises a luminescent moiety, an optically-active moiety, a self-quenching dye, or a proximity quenching dye.

12. The method of claim 11, wherein said labeling reagent comprises a dye that is functionalized with an iodoacetamide moiety.

13. The method of claim 11, wherein said labeling reagent comprises a bimane derivative.

14. The method of claim 13, wherein said bimane derivative is monobromobimane.

15. The method of claim 1, wherein said converting in (d) comprises providing to said growing nucleic acid strand one or more of a metal ion, an oxidant, an oxime, or a reducing agent.

16. The method of claim 15, wherein said converting in (d) comprises providing to said growing nucleic acid strand said metal ion selected from the group consisting of a silver-, mercury- and lead-containing ion.

17. A method for determining a sequence of a template nucleic acid molecule, comprising:
   (a) contacting a nucleotide analog with a growing nucleic acid strand having sequence complementarity with said template nucleic acid molecule, under conditions sufficient to incorporate said nucleotide analog into said growing nucleic acid strand, wherein said nucleotide analog comprises a modified phosphate group comprising sulfur or selenium;
   (b) reacting said modified phosphate group of said nucleotide analog with a labeling reagent comprising a label to generate a label-S-P, label-S-S-P, or label-Se-P group on said growing nucleic acid strand;
   (c) detecting one or more signals indicative of said label; and
   (d) converting said label-S-P, label-S-S-P, or label-Se-P group to an O=P group on said growing nucleic acid strand; wherein said converting in (d) comprises providing to said growing nucleic acid strand one or more of a metal ion, an oxidant, an oxime, or a reducing agent; wherein said oxidant selected from the group consisting of iodine, iodosobenzoate, and potassium peroxymonosulfate (oxone).

18. A method for determining a sequence of a template nucleic acid molecule, comprising:
    (a) contacting a nucleotide analog with a growing nucleic acid strand having sequence complementarity with said template nucleic acid molecule, under conditions sufficient to incorporate said nucleotide analog into said growing nucleic acid strand, wherein said nucleotide analog comprises a modified phosphate group comprising sulfur or selenium;
    (b) reacting said modified phosphate group of said nucleotide analog with a labeling reagent comprising a label to generate a label-S-P, label-S-S-P, or label-Se-P group on said growing nucleic acid strand;
    (c) detecting one or more signals indicative of said label; and
    (d) converting said label-S-P, label-S-S-P, or label-Se-P group to an O=P group on said growing nucleic acid strand; wherein said converting in (d) comprises providing to said growing nucleic acid strand one or more of a metal ion, an oxidant, an oxime, or a reducing agent; wherein said oxime selected from the group consisting of 2-pyridine aldoxime, 4-pyridine aldoxime, obidoxime, HI-6, HLö-7, E-2-nitrobenzaldoxime, and E-4-nitrobenzldoxime.

19. The method of claim 15, wherein said converting in (d) comprises providing to said growing nucleic acid strand said reducing agent selected from the group consisting of Tris(2-carboxyethyl phosphine (TCEP), tris(hydroxypropyl) phosphine (THP), and dithiothreitol (DTT).

20. The method of claim 1, wherein said reacting in (b) comprises an alkylation reaction between said labeling reagent and said modified phosphate group.

21. The method of claim 1, wherein the label comprises a dye and a functional group configured to react to said modified phosphate group.

22. The method of claim 21, wherein the functional group configured to react to said modified phosphate group comprises iodoacetamide.

23. The method of claim 21, wherein the functional group configured to react to said modified phosphate group comprises an alkylating agent.

* * * * *

SEQUENCE LISTING

```
<160> NUMBER OF SEQ ID NOS: 8

<210> SEQ ID NO 1
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gatcgttcgc gcacgcgacg ttcagcgcag cgcgattcga cagcagcgca ttcacagcgc    60
gcgcaactga gtcggagaca cgcagggatg agatgg                              96

<210> SEQ ID NO 2
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 2
ccatctcatc cctgcgtgtc tccgac                                           26

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttttttttt ttgtctccga ctcagttgcg cgcgctgtga a                          41

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tttttttttt tttttttttt tttagttgcg cgcgctgtga atgcgctgct g               51

<210> SEQ ID NO 5
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttttttttt tttttttttt tttttttttt ttgctgtgaa tgcgctgctg tcgaatcgcg      60
c                                                                      61

<210> SEQ ID NO 6
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tttttttttt tttttttttt tttttttttt tttttttttt tttttcgaat cgcgctgcgc      60
tgaacgtcgc g                                                           71

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccatctcatc cctgcgtgtc tccgact                                          27

<210> SEQ ID NO 8
```

```
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttgcttgctt gcttgcactg agtcggagac acgcagggat gagatgg                  47
```